United States Patent
Koop

(10) Patent No.: US 10,238,882 B2
(45) Date of Patent: *Mar. 26, 2019

(54) SYSTEMS AND METHODS FOR TREATING CARDIAC ARRHYTHMIAS

(71) Applicant: CARDIAC PACEMAKERS, INC., St. Paul, MN (US)

(72) Inventor: Brendan E. Koop, Ham Lake, MN (US)

(73) Assignee: CARDIAC PACEMAKERS, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/587,033

(22) Filed: May 4, 2017

(65) Prior Publication Data

US 2017/0232266 A1 Aug. 17, 2017

Related U.S. Application Data

(63) Continuation of application No. 15/012,443, filed on Feb. 1, 2016, now Pat. No. 9,669,230.
(Continued)

(51) Int. Cl.
*A61B 5/00* (2006.01)
*A61N 1/39* (2006.01)
(Continued)

(52) U.S. Cl.
CPC ............ *A61N 1/3962* (2013.01); *A61B 5/042* (2013.01); *A61B 5/046* (2013.01); *A61B 5/0464* (2013.01);
(Continued)

(58) Field of Classification Search
CPC .. A61N 1/3962; A61N 1/3624; A61N 1/3987; A61N 1/3925; A61N 1/3621;
(Continued)

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

"Instructions for Use System 1, Leadless Cardiac Pacemaker (LCP) and Delivery Catheter," Nanostim Leadless Pacemakers, pp. 1-28, 2013.

(Continued)

*Primary Examiner* — Catherine M Voorhees
(74) *Attorney, Agent, or Firm* — Seager, Tufte & Wickhem LLP

(57) ABSTRACT

Systems and methods for treating cardiac arrhythmias are disclosed. In one embodiment, an SICD comprises two or more electrodes, a charge storage device, and a controller operatively coupled to two or more of the electrodes and the charge storage device. In some embodiments, the controller is configured to monitor cardiac activity of the heart of the patient, detect an occurrence of a cardiac arrhythmia based on the cardiac activity, and determine a type of the detected cardiac arrhythmia from two or more types of cardiac arrhythmias. If the determined type of cardiac arrhythmia is one of a first set of cardiac arrhythmia types, the controller sends an instruction for reception by an LCP to initiate the application of ATP therapy by the LCP. If the determined type of cardiac arrhythmia is not one of the first set cardiac arrhythmia types, the controller does not send the instruction.

20 Claims, 8 Drawing Sheets

Related U.S. Application Data

(60) Provisional application No. 62/113,173, filed on Feb. 6, 2015.

(51) Int. Cl.
*A61B 5/042* (2006.01)
*A61N 1/362* (2006.01)
*A61B 5/046* (2006.01)
*A61N 1/372* (2006.01)
*A61N 1/375* (2006.01)
*A61B 5/0452* (2006.01)
*A61B 5/0464* (2006.01)

(52) U.S. Cl.
CPC .......... *A61B 5/04525* (2013.01); *A61B 5/686* (2013.01); *A61B 5/7246* (2013.01); *A61N 1/3621* (2013.01); *A61N 1/3624* (2013.01); *A61N 1/3756* (2013.01); *A61N 1/37288* (2013.01); *A61N 1/3925* (2013.01); *A61N 1/3987* (2013.01); *A61N 1/37205* (2013.01); *A61N 1/37217* (2013.01)

(58) Field of Classification Search
CPC .............. A61N 1/3756; A61N 1/37288; A61N 1/37205; A61N 1/37127; A61B 5/042; A61B 5/686; A61B 5/046; A61B 5/7246; A61B 5/0464; A61B 5/04525
See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,333,470 A | 6/1982 | Barthel |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,531,527 A | 7/1985 | Reinhold, Jr. et al. |
| 4,539,999 A | 9/1985 | Mans |
| 4,556,063 A | 12/1985 | Thompson et al. |
| 4,562,841 A | 1/1986 | Brockway et al. |
| 4,585,004 A | 4/1986 | Brownlee |
| 4,589,420 A | 5/1986 | Adams et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| RE32,378 E | 3/1987 | Barthel |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,884,345 A | 12/1989 | Long |
| 4,886,064 A | 12/1989 | Strandberg |
| 4,924,875 A | 5/1990 | Chamoun |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,000,189 A | 3/1991 | Throne et al. |
| 5,002,052 A | 3/1991 | Haluska |
| 5,012,806 A | 5/1991 | De Bellis |
| 5,014,698 A | 5/1991 | Cohen |
| 5,036,849 A | 8/1991 | Hauck et al. |
| 5,058,581 A | 10/1991 | Silvian |
| 5,078,134 A | 1/1992 | Heilman et al. |
| 5,107,850 A | 4/1992 | Olive |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,139,028 A | 8/1992 | Steinhaus et al. |
| 5,144,950 A | 9/1992 | Stoop et al. |
| 5,156,148 A | 10/1992 | Cohen |
| 5,161,527 A | 11/1992 | Nappholz et al. |
| 5,170,784 A | 12/1992 | Ramon et al. |
| 5,179,945 A | 1/1993 | Von Hofwegen et al. |
| 5,193,539 A | 3/1993 | Schulman et al. |
| 5,193,540 A | 3/1993 | Schulman et al. |
| 5,193,550 A | 3/1993 | Duffin |
| 5,205,283 A | 4/1993 | Olson |
| 5,215,098 A | 6/1993 | Steinhaus et al. |
| 5,217,021 A | 6/1993 | Steinhaus et al. |
| 5,241,961 A | 9/1993 | Henry |
| 5,243,977 A | 9/1993 | Trabucco et al. |
| 5,255,186 A | 10/1993 | Steinhaus et al. |
| 5,265,602 A | 11/1993 | Anderson et al. |
| 5,269,326 A | 12/1993 | Verrier |
| 5,271,411 A | 12/1993 | Ripley et al. |
| 5,273,049 A | 12/1993 | Steinhaus et al. |
| 5,275,621 A | 1/1994 | Mehra |
| 5,284,136 A | 2/1994 | Hauck et al. |
| 5,292,348 A | 3/1994 | Saumarez et al. |
| 5,300,107 A | 4/1994 | Stokes et al. |
| 5,301,677 A | 4/1994 | Hsung |
| 5,312,439 A | 5/1994 | Loeb |
| 5,312,445 A | 5/1994 | Nappholz et al. |
| 5,313,953 A | 5/1994 | Yomtov et al. |
| 5,314,459 A | 5/1994 | Swanson et al. |
| 5,318,597 A | 6/1994 | Hauck et al. |
| 5,324,310 A | 6/1994 | Greeninger et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,360,436 A | 11/1994 | Alt et al. |
| 5,366,487 A | 11/1994 | Adams et al. |
| 5,372,606 A | 12/1994 | Lang et al. |
| 5,376,106 A | 12/1994 | Stahmann et al. |
| 5,378,775 A | 1/1995 | Shimizu et al. |
| 5,379,775 A | 1/1995 | Kruse |
| 5,379,776 A | 1/1995 | Murphy et al. |
| 5,383,915 A | 1/1995 | Adams |
| 5,388,578 A | 2/1995 | Yomtov et al. |
| 5,400,795 A | 3/1995 | Murphy et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,447,524 A | 9/1995 | Alt |
| 5,448,997 A | 9/1995 | Kruse et al. |
| 5,456,261 A | 10/1995 | Luczyk |
| 5,456,691 A | 10/1995 | Snell |
| 5,458,623 A | 10/1995 | Lu et al. |
| 5,466,246 A | 11/1995 | Silvian |
| 5,468,254 A | 11/1995 | Hahn et al. |
| 5,503,160 A | 4/1996 | Pering et al. |
| 5,509,927 A | 4/1996 | Epstein et al. |
| 5,520,191 A | 5/1996 | Karlsson et al. |
| 5,522,866 A | 6/1996 | Fernald |
| 5,531,767 A | 7/1996 | Fain |
| 5,540,727 A | 7/1996 | Tockman et al. |
| 5,545,186 A | 8/1996 | Olson et al. |
| 5,545,202 A | 8/1996 | Dahl et al. |

(56) References Cited

U.S. PATENT DOCUMENTS

| | | |
|---|---|---|
| 5,591,214 A | 1/1997 | Lu |
| 5,620,466 A | 4/1997 | Haefner et al. |
| 5,620,471 A | 4/1997 | Duncan |
| 5,630,425 A | 5/1997 | Panescu et al. |
| 5,634,468 A | 6/1997 | Platt et al. |
| 5,634,938 A | 6/1997 | Swanson et al. |
| 5,645,070 A | 7/1997 | Turcott |
| 5,662,688 A | 9/1997 | Haefner et al. |
| 5,674,259 A | 10/1997 | Gray et al. |
| 5,682,900 A | 11/1997 | Arand et al. |
| 5,683,425 A | 11/1997 | Hauptmann |
| 5,683,426 A | 11/1997 | Greenhut et al. |
| 5,683,432 A | 11/1997 | Goedeke et al. |
| 5,712,801 A | 1/1998 | Turcott |
| 5,713,367 A | 2/1998 | Arnold et al. |
| 5,713,932 A | 2/1998 | Gillberg et al. |
| 5,720,770 A | 2/1998 | Nappholz et al. |
| 5,728,154 A | 3/1998 | Crossett et al. |
| 5,738,105 A | 4/1998 | Kroll |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,766,225 A | 6/1998 | Kramm |
| 5,774,501 A | 6/1998 | Halpern et al. |
| 5,776,168 A | 7/1998 | Gunderson |
| 5,779,645 A | 7/1998 | Olson et al. |
| 5,792,065 A | 8/1998 | Xue et al. |
| 5,792,202 A | 8/1998 | Reuter |
| 5,792,203 A | 8/1998 | Schroeppel |
| 5,792,205 A | 8/1998 | Alt et al. |
| 5,792,208 A | 8/1998 | Gray |
| 5,795,303 A | 8/1998 | Swanson et al. |
| 5,814,089 A | 9/1998 | Stokes et al. |
| 5,817,133 A | 10/1998 | Houben |
| 5,819,741 A | 10/1998 | Karlsson et al. |
| 5,827,197 A | 10/1998 | Bocek et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,848,972 A | 12/1998 | Triedman et al. |
| 5,855,593 A | 1/1999 | Olson et al. |
| 5,857,977 A | 1/1999 | Caswell et al. |
| 5,873,894 A | 2/1999 | Vandegriff et al. |
| 5,873,897 A | 2/1999 | Armstrong et al. |
| 5,891,170 A | 4/1999 | Nitzsche et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,935,081 A | 8/1999 | Kadhiresan |
| 5,941,906 A | 8/1999 | Barreras et al. |
| 5,954,662 A | 9/1999 | Swanson et al. |
| 5,954,757 A | 9/1999 | Gray |
| 5,978,707 A | 11/1999 | Krig et al. |
| 5,978,713 A | 11/1999 | Prutchi et al. |
| 5,991,660 A | 11/1999 | Goyal |
| 5,999,848 A | 12/1999 | Gord et al. |
| 5,999,857 A | 12/1999 | Weijand et al. |
| 6,026,320 A | 2/2000 | Carlson et al. |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach et al. |
| 6,080,187 A | 6/2000 | Alt et al. |
| 6,083,248 A | 7/2000 | Thompson |
| 6,106,551 A | 8/2000 | Crossett et al. |
| 6,108,578 A | 8/2000 | Bardy et al. |
| 6,115,636 A | 9/2000 | Ryan |
| 6,141,581 A | 10/2000 | Olson et al. |
| 6,141,588 A | 10/2000 | Cox et al. |
| 6,141,592 A | 10/2000 | Pauly et al. |
| 6,144,879 A | 11/2000 | Gray |
| 6,151,524 A | 11/2000 | Krig et al. |
| 6,162,195 A | 12/2000 | Igo et al. |
| 6,164,284 A | 12/2000 | Schulman et al. |
| 6,167,310 A | 12/2000 | Grevious |
| 6,169,918 B1 | 1/2001 | Haefner et al. |
| 6,178,350 B1 | 1/2001 | Olson et al. |
| 6,179,865 B1 | 1/2001 | Hsu et al. |
| 6,208,894 B1 | 3/2001 | Schulman et al. |
| 6,211,799 B1 | 4/2001 | Post et al. |
| 6,212,428 B1 | 4/2001 | Hsu et al. |
| 6,221,011 B1 | 4/2001 | Bardy |
| 6,223,078 B1 | 4/2001 | Marcovecchio |
| 6,230,055 B1 | 5/2001 | Sun et al. |
| 6,230,059 B1 | 5/2001 | Duffin |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,554 B1 | 7/2001 | Hsu et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,275,732 B1 | 8/2001 | Hsu et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,298,271 B1 | 10/2001 | Weijand |
| 6,308,095 B1 | 10/2001 | Hsu et al. |
| 6,312,378 B1 | 11/2001 | Bardy |
| 6,312,388 B1 | 11/2001 | Marcovecchio et al. |
| 6,315,721 B2 | 11/2001 | Schulman et al. |
| 6,317,632 B1 | 11/2001 | Krig et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,405,083 B1 | 6/2002 | Rockwell et al. |
| 6,409,674 B1 | 6/2002 | Brockway et al. |
| 6,411,848 B2 | 6/2002 | Kramer et al. |
| 6,424,865 B1 | 7/2002 | Ding |
| 6,430,435 B1 | 8/2002 | Hsu et al. |
| 6,434,417 B1 | 8/2002 | Lovett |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,449,503 B1 | 9/2002 | Hsu |
| 6,453,200 B1 | 9/2002 | Koslar |
| 6,456,871 B1 | 9/2002 | Hsu et al. |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,477,404 B1 | 11/2002 | Yonce et al. |
| 6,480,733 B1 | 11/2002 | Turcott |
| 6,480,745 B2 | 11/2002 | Nelson et al. |
| 6,484,055 B1 | 11/2002 | Marcovecchio |
| 6,487,443 B2 | 11/2002 | Olson et al. |
| 6,490,487 B1 | 12/2002 | Kraus et al. |

(56) References Cited

U.S. PATENT DOCUMENTS

| | | |
|---|---|---|
| 6,493,579 B1 | 12/2002 | Gilkerson et al. |
| 6,505,067 B1 | 1/2003 | Lee et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,522,917 B1 | 2/2003 | Hsu et al. |
| 6,522,925 B1 | 2/2003 | Gilkerson et al. |
| 6,526,311 B2 | 2/2003 | Begemann |
| 6,526,313 B2 | 2/2003 | Sweeney et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,658,283 B1 | 12/2003 | Bornzin et al. |
| 6,658,286 B2 | 12/2003 | Seim |
| 6,666,844 B1 | 12/2003 | Igo et al. |
| 6,671,548 B1 | 12/2003 | Mouchawar et al. |
| 6,687,540 B2 | 2/2004 | Marcovecchio |
| 6,689,117 B2 | 2/2004 | Sweeney et al. |
| 6,690,959 B2 | 2/2004 | Thompson |
| 6,704,602 B2 | 3/2004 | Berg et al. |
| 6,708,058 B2 | 3/2004 | Kim et al. |
| 6,718,204 B2 | 4/2004 | DeGroot et al. |
| 6,718,212 B2 | 4/2004 | Parry et al. |
| 6,721,597 B1 | 4/2004 | Bardy et al. |
| 6,728,572 B2 | 4/2004 | Hsu et al. |
| 6,738,670 B1 | 5/2004 | Almendinger et al. |
| 6,745,068 B2 | 6/2004 | Koyrakh et al. |
| 6,749,566 B2 | 6/2004 | Russ |
| 6,758,810 B2 | 7/2004 | Lebel et al. |
| 6,760,615 B2 | 7/2004 | Ferek-Petric |
| 6,763,269 B2 | 7/2004 | Cox |
| 6,766,190 B2 | 7/2004 | Ferek-Petric |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,889,081 B2 | 5/2005 | Hsu |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,959,212 B2 | 10/2005 | Hsu et al. |
| 6,978,176 B2 | 12/2005 | Lattouf |
| 6,978,177 B1 | 12/2005 | Chen et al. |
| 6,985,773 B2 | 1/2006 | Von Arx et al. |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,031,764 B2 | 4/2006 | Schwartz et al. |
| 7,039,463 B2 | 5/2006 | Marcovecchio |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,110,824 B2 | 9/2006 | Amundson et al. |
| 7,120,504 B2 | 10/2006 | Osypka |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,203,535 B1 | 4/2007 | Hsu et al. |
| 7,206,423 B1 | 4/2007 | Feng et al. |
| 7,209,790 B2 | 4/2007 | Thompson et al. |
| 7,212,849 B2 | 5/2007 | Zhang et al. |
| 7,212,871 B1 | 5/2007 | Morgan |
| 7,226,440 B2 | 6/2007 | Gelfand et al. |
| 7,228,176 B2 | 6/2007 | Smith et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,433 B1 | 8/2007 | Falkenberg et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,956 B2 | 4/2009 | Thompson |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |

(56) References Cited

U.S. PATENT DOCUMENTS

| | | |
|---|---|---|
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,751,890 B2 | 7/2010 | McCabe et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzenne et al. |
| 7,890,192 B1 | 2/2011 | Kelsch et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding et al. |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 3,010,209 A1 | 8/2011 | Jacobson |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 3,019,419 A1 | 9/2011 | Panescu et al. |
| 3,019,434 A1 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,131,360 B2 | 3/2012 | Perschbacher et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,170,663 B2 | 5/2012 | DeGroot et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,233,985 B2 | 7/2012 | Bulkes et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |

(56) References Cited

U.S. PATENT DOCUMENTS

| | | |
|---|---|---|
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,527,068 B2 | 9/2013 | Ostroff |
| 8,532,790 B2 | 9/2013 | Griswold |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang et al. |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,773 B2 | 5/2014 | Willis et al. |
| 8,738,147 B2 | 5/2014 | Hastings et al. |
| 8,744,572 B1 | 6/2014 | Greenut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,500 B2 | 12/2014 | Smith et al. |
| 8,903,513 B2 | 12/2014 | Ollivier |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,669,230 B2 * | 6/2017 | Koop .................. A61N 1/3624 |
| 2002/0002389 A1 | 1/2002 | Bradley et al. |
| 2002/0032469 A1 | 3/2002 | Marcovecchio |
| 2002/0032470 A1 | 3/2002 | Linberg |
| 2002/0035335 A1 | 3/2002 | Schauerte |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049474 A1 | 4/2002 | Marcovecchio et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0072778 A1 | 6/2002 | Guck et al. |
| 2002/0082665 A1 | 6/2002 | Haller et al. |
| 2002/0087091 A1 | 7/2002 | Koyrakh et al. |
| 2002/0091333 A1 | 7/2002 | Hsu et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107552 A1 | 8/2002 | Krig et al. |
| 2002/0107559 A1 | 8/2002 | Sanders et al. |
| 2002/0120299 A1 | 8/2002 | OStroff et al. |
| 2002/0123768 A1 | 9/2002 | Gilkerson et al. |
| 2002/0123769 A1 | 9/2002 | Panken et al. |

(56) References Cited

U.S. PATENT DOCUMENTS

| | | |
|---|---|---|
| 2002/0123770 A1 | 9/2002 | Combs et al. |
| 2002/0143370 A1 | 10/2002 | Kim |
| 2002/0147407 A1 | 10/2002 | Seim |
| 2002/0147474 A1 | 10/2002 | Seim et al. |
| 2002/0173830 A1 | 11/2002 | Starkweather et al. |
| 2002/0183637 A1 | 12/2002 | Kim et al. |
| 2002/0183639 A1 | 12/2002 | Sweeney et al. |
| 2002/0193846 A1 | 12/2002 | Pool et al. |
| 2002/0198461 A1 | 12/2002 | Hsu et al. |
| 2003/0004552 A1 | 1/2003 | Plombon et al. |
| 2003/0009203 A1 | 1/2003 | Lebel et al. |
| 2003/0028082 A1 | 2/2003 | Thompson |
| 2003/0041866 A1 | 3/2003 | Linberg et al. |
| 2003/0050563 A1 | 3/2003 | Suribhotla et al. |
| 2003/0060849 A1 | 3/2003 | Hsu |
| 2003/0069609 A1 | 4/2003 | Thompson |
| 2003/0083586 A1 | 5/2003 | Ferek-Petric |
| 2003/0083587 A1 | 5/2003 | Ferek-Petric |
| 2003/0088278 A1 | 5/2003 | Bardy et al. |
| 2003/0097153 A1 | 5/2003 | Bardy et al. |
| 2003/0100923 A1 | 5/2003 | Bjorling et al. |
| 2003/0105491 A1 | 6/2003 | Gilkerson et al. |
| 2003/0109792 A1 | 6/2003 | Hsu et al. |
| 2003/0114889 A1 | 6/2003 | Huvelle et al. |
| 2003/0114908 A1 | 6/2003 | Flach |
| 2003/0120316 A1 | 6/2003 | Spinelli et al. |
| 2003/0144701 A1 | 7/2003 | Mehra et al. |
| 2003/0181818 A1 | 9/2003 | Kim et al. |
| 2003/0187460 A1 | 10/2003 | Chin et al. |
| 2003/0187461 A1 | 10/2003 | Chin |
| 2003/0208238 A1 | 11/2003 | Weinberg et al. |
| 2004/0015090 A1 | 1/2004 | Sweeney et al. |
| 2004/0024435 A1 | 2/2004 | Leckrone et al. |
| 2004/0077995 A1 | 4/2004 | Ferek-Petric et al. |
| 2004/0087938 A1 | 5/2004 | Leckrone et al. |
| 2004/0088035 A1 | 5/2004 | Guenst et al. |
| 2004/0093035 A1 | 5/2004 | Schwartz et al. |
| 2004/0102830 A1 | 5/2004 | Williams |
| 2004/0116820 A1 | 6/2004 | Daum et al. |
| 2004/0116972 A1 | 6/2004 | Marcovecchio |
| 2004/0127806 A1 | 7/2004 | Sweeney et al. |
| 2004/0127959 A1 | 7/2004 | Amundson et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176694 A1 | 9/2004 | Kim et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0267303 A1 | 12/2004 | Guenst |
| 2005/0010257 A1 | 1/2005 | Lincoln et al. |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149134 A1 | 7/2005 | McCabe et al. |
| 2005/0149135 A1 | 7/2005 | Krig et al. |
| 2005/0149138 A1 | 7/2005 | Min et al. |
| 2005/0159781 A1 | 7/2005 | Hsu |
| 2005/0165466 A1 | 7/2005 | Morris et al. |
| 2005/0182465 A1 | 8/2005 | Ness |
| 2005/0197674 A1 | 9/2005 | McCabe et al. |
| 2005/0203410 A1 | 9/2005 | Jenkins |
| 2005/0256544 A1 | 11/2005 | Thompson |
| 2005/0283208 A1 | 12/2005 | Von Arx et al. |
| 2006/0009831 A1 | 1/2006 | Lau et al. |
| 2006/0015148 A1 | 1/2006 | McCabe et al. |
| 2006/0025822 A1* | 2/2006 | Zhang ............... A61N 1/3622 607/4 |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0074330 A1 | 4/2006 | Smith et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0122527 A1 | 6/2006 | Marcovecchio |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0173498 A1 | 8/2006 | Banville et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2006/0281998 A1 | 12/2006 | Li |
| 2007/0004979 A1 | 1/2007 | Wojciechowicz et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |

(56) References Cited

U.S. PATENT DOCUMENTS

| | | |
|---|---|---|
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0078322 A1 | 3/2012 | Del Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172941 A1 | 7/2012 | Rys |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0030487 A1 | 1/2013 | Keel et al. |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bomzin et al. |
| 2013/0150695 A1 | 6/2013 | Biela et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0267826 A1 | 10/2013 | Sison |
| 2013/0268042 A1 | 10/2013 | Hastings et al. |
| 2013/0274828 A1 | 10/2013 | Willis |

(56) References Cited

U.S. PATENT DOCUMENTS

| | | |
|---|---|---|
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0257324 A1 | 9/2014 | Fain |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0330326 A1* | 11/2014 | Thompson-Nauman ........ A61N 1/3918 607/4 |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0228701 A1 | 8/2016 | Huelskamp et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0253505 A2 | 1/1988 |
| EP | 0308536 A1 | 3/1989 |
| EP | 0360412 A1 | 3/1990 |
| EP | 0362611 A1 | 4/1990 |
| EP | 0401962 A2 | 12/1990 |
| EP | 0469817 A2 | 2/1992 |
| EP | 503823 A2 | 9/1992 |
| EP | 0506230 A1 | 9/1992 |
| EP | 0554208 A2 | 8/1993 |
| EP | 0597459 A2 | 5/1994 |
| EP | 0617980 A2 | 10/1994 |
| EP | 0711531 A1 | 5/1996 |
| EP | 0744190 A2 | 11/1996 |
| EP | 0748638 A2 | 12/1996 |
| EP | 0784996 A1 | 7/1997 |
| EP | 0848965 A2 | 6/1998 |
| EP | 0879621 A2 | 11/1998 |
| EP | 0919256 A1 | 6/1999 |
| EP | 1112756 A2 | 7/2001 |
| EP | 0993842 A1 | 4/2004 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008528103 | 7/2008 |
| JP | 2008540040 A | 11/2008 |
| JP | 2009511214 A | 3/2009 |
| JP | 5199867 B2 | 2/2013 |
| WO | 9302746 A1 | 2/1993 |
| WO | 9401173 A1 | 1/1994 |
| WO | 9500202 A1 | 1/1995 |
| WO | 9636134 A1 | 11/1996 |
| WO | 9739681 A1 | 10/1997 |
| WO | 9739799 A1 | 10/1997 |
| WO | 9825669 A1 | 6/1998 |
| WO | 9826840 A1 | 6/1998 |
| WO | 9840010 A1 | 9/1998 |

(56) References Cited

FOREIGN PATENT DOCUMENTS

| | | |
|---|---|---|
| WO | 9848891 A1 | 11/1998 |
| WO | 9853879 A1 | 12/1998 |
| WO | 9915232 A1 | 4/1999 |
| WO | 9939767 A1 | 8/1999 |
| WO | 0053089 A1 | 9/2000 |
| WO | 0059573 A1 | 10/2000 |
| WO | 0113993 A1 | 3/2001 |
| WO | 0126733 A1 | 4/2001 |
| WO | 2011063848 A1 | 6/2001 |
| WO | 0234330 A2 | 1/2003 |
| WO | 02098282 A2 | 5/2003 |
| WO | 03047690 A2 | 6/2003 |
| WO | 2005000206 A3 | 4/2005 |
| WO | 2005042089 A1 | 5/2005 |
| WO | 2005089643 A1 | 9/2005 |
| WO | 2006020198 A2 | 2/2006 |
| WO | 2006020198 A3 | 5/2006 |
| WO | 2006049767 A1 | 5/2006 |
| WO | 2006086435 A3 | 8/2006 |
| WO | 2006113659 A1 | 10/2006 |
| WO | 2006124833 A2 | 11/2006 |
| WO | 2007033226 A2 | 3/2007 |
| WO | 2007047681 A2 | 4/2007 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

Duru et al., "The Potential for Inappropriate Ventricular Tachycardia Confirmation Using the Intracardiac Electrogram (EGM) Width Criterion", Pacing and Clinical Electrophysiology [PACE], 22(7): 1039-1046, Jul. 1999.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Hughes et al., "The Effects of Electrode Position on the Detection of the Transvenous Cardiac Electrogram", PACE, 3(6): 651-655, Nov. 1980.

International Search Report and Written Opinion for Application No. PCT/US2005/035057, 17 pages, dated Feb. 1, 2006.

Kinoshita et al., "Letter to the Editor", Journal of Electrocardiology, 29(3): 255-256, Jul. 1996.

Leitch et al., "Feasibility of an Implantable Arrhythmia Monitor", PACE, 15(12): 2232-2235, Dec. 1992.

Mazur et al., "Functional Similarity Between Electrograms Recorded from an Implantable Cardioverter Defibrillator Emulator and the Surface Electrocardiogram", PACE, 24(1): 34-40, Jan. 2001.

Medtronic, "Marquis™ DR 7274 Dual Chamber Implantable Cardioverter Defibrillator", Reference Manual, 426 pgs., Feb. 2002.

Morris et al., "Detection of Atrial Arrhythmia for Cardiac Rhythm Management by Implantable Devices", Journal of Electrocardiology, vol. 33, Supplement 1, pp. 133-139, 2000.

Notification of Transmittal of the International Search Report and the Written Opinion of the International Searching Authority, or the Declaration, dated Feb. 24, 2016, 10 pages.

Notification of Transmittal of the International Search Report and the Written Opinion of the International Searching Authority, or the Declaration, dated Jan. 29, 2016, 15 pages.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(3&4): 324-331, 1970.

Theres et al., "Electrogram Signals Recorded from Acute and Chronic Pacemaker Implantation Sites in Pacemaker Patients", PACE, 21(1): 11-17, Jan. 1998.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration for Application No. PCT/US2016/015991, 2016, 10 pages, dated May 2, 2016.

U.S. Pat. No. 8,886,318, filed Nov. 2014, Jacobson et al. (withdrawn).

Office Action Application No. 2017-540731 6 pages, dated Jun. 12, 2018.

* cited by examiner

SYSTEMS AND METHODS FOR TREATING CARDIAC ARRHYTHMIAS

This is a continuation of co-pending U.S. patent application Ser. No. 15/012,443, filed Feb. 1, 2016, which claims the benefit of U.S. Provisional Patent Application Ser. No. 62/113,173 filed on Feb. 6, 2015, both of which are incorporated herein by reference.

TECHNICAL FIELD

The present disclosure generally relates to systems, devices, and methods for treating cardiac arrhythmias, and more particularly, to systems, devices, and methods for detecting cardiac arrhythmias and coordinating therapy between multiple devices.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) have been implanted in a patient's body. Such devices may monitor and provide electrical stimulation to the heart to help the heart operate in a more normal, efficient and/or safe manner. In some cases, a patient may have multiple implanted devices.

SUMMARY

The present disclosure generally relates to systems, devices, and methods for treating cardiac arrhythmias, and more particularly, to systems, devices, and methods for detecting cardiac arrhythmias and coordinating treatment of anti-tachycardia pacing (ATP) therapy and defibrillation shock therapy between a leadless cardiac pacemaker and another medical device.

In one embodiment, a subcutaneous implantable cardioverter defibrillator (SICD) for delivering a defibrillation shock to a heart of a patient comprises two or more electrodes, a charge storage device for storing a charge that can be delivered to shock the heart via two or more of the electrodes, and a controller operatively coupled to two or more of the electrodes and the charge storage device. The controller may be configured to monitor cardiac activity of the heart of the patient via cardiac signals received via two or more of the electrodes, detect an occurrence of a cardiac arrhythmia based on the cardiac activity, and determine a type of the detected cardiac arrhythmia from two or more types of cardiac arrhythmias. If the determined type of cardiac arrhythmia is one of a first set of cardiac arrhythmia types, the controller may send an instruction via two or more of the electrodes for reception by a Leadless Cardiac Pacemaker (LCP) to initiate the application of ATP therapy by the LCP. If the determined type of cardiac arrhythmia is not one of the first set cardiac arrhythmia types, the controller may not send the instruction.

Additionally, or alternatively, in the previous embodiment, the instruction may also include one or more ATP parameters that define one or more characteristics of the ATP therapy.

Additionally, or alternatively, in any of the previous embodiments, the one or more characteristics of the ATP therapy may comprise a method of ATP therapy.

Additionally, or alternatively, in any of the previous embodiments, the one or more characteristics of the ATP therapy may comprise a number of ATP bursts applied during the ATP therapy.

Additionally, or alternatively, in any of the previous embodiments, the controller may further be configured to initiate charging of the charge storage device if the determined type of the cardiac arrhythmia is one of a second set cardiac arrhythmia types, and wait to initiate charging of the charge storage device if the determined type of the cardiac arrhythmia is one of the first set of cardiac arrhythmia types.

Additionally, or alternatively, in any of the previous embodiments, if an instruction was sent to initiate the application of ATP therapy by the LCP, the controller may be further configured to determine if the application of the ATP therapy by the LCP was successful in terminating the cardiac arrhythmia, and if so, not initiate charging of the charge storage device if the determined type of the cardiac arrhythmia is one of the first set of cardiac arrhythmia types.

Additionally, or alternatively, in any of the previous embodiments, if an instruction was sent to initiate the application of ATP therapy by the LCP, the controller may be further configured to determine if the application of the ATP therapy by the LCP was successful in terminating the cardiac arrhythmia, and if so, terminate the charging of the charge storage device if the determined type of the cardiac arrhythmia is one of the second cardiac arrhythmia types.

Additionally, or alternatively, in any of the previous embodiments, the first set of type of cardiac arrhythmia types may include Monomorphic Ventricular Tachycardia (MVT).

Additionally, or alternatively, in any of the previous embodiments, the second set of cardiac arrhythmia types may include one or more of Polymorphic Ventricular Tachycardia (PVT), Supra Ventricular Tachycardia (SVT), and Ventricular Fibrillation (VF).

Additionally, or alternatively, in any of the previous embodiments, the second set of cardiac arrhythmia types may include Polymorphic Ventricular Tachycardia (PVT).

Additionally, or alternatively, in any of the previous embodiments, the second set of cardiac arrhythmia types may include Supra Ventricular Tachycardia (SVT).

Additionally, or alternatively, in any of the previous embodiments, the second set of cardiac arrhythmia types may include Monomorphic Ventricular Tachycardia (MVT).

Additionally, or alternatively, in any of the previous embodiments, the first set of cardiac arrhythmia types and the second set of cardiac arrhythmia types may share one or more common cardiac arrhythmia types, but this is not required.

Additionally, or alternatively, in any of the previous embodiments, the cardiac arrhythmia types in the first set of cardiac arrhythmia types may be user selectable.

Additionally, or alternatively, in any of the previous embodiments, the SICD may further comprise an energy storage module, and the cardiac arrhythmia types in the first set of cardiac arrhythmia types may depend at least partially on a charge level of the storage module.

Additionally, or alternatively, in any of the previous embodiments, to determine a type of the detected cardiac arrhythmia from two or more types of cardiac arrhythmias, the controller may be configured to compare the cardiac signals to one or more templates of cardiac signals.

In another embodiment, a subcutaneous implantable cardioverter defibrillator (SICD) for delivering a defibrillation shock to a heart of a patient may comprise two or more electrodes, a charge storage device for storing a charge that can be delivered to shock the heart via two or more of the electrodes, and a controller operatively coupled to two or more of the electrodes and the charge storage device. The controller may be configured to monitor cardiac activity of the heart of the patient via cardiac signals received via two or more of the electrodes, detect an occurrence of a cardiac arrhythmia based on the cardiac activity; and determine a type of the detected cardiac arrhythmia from two or more types of cardiac arrhythmias. If the determined type of cardiac arrhythmia is one of a first set of cardiac arrhythmia types, the controller may send an instruction via two or more of the electrodes for reception by a Leadless Cardiac Pacemaker (LCP) to initiate the application of ATP therapy by the LCP. If the determined type of cardiac arrhythmia is not one of the first set of cardiac arrhythmia types, the controller may not send the instruction.

Additionally, or alternatively, in the previous embodiment, the instruction may also include one or more ATP parameters that define one or more characteristics of the ATP therapy.

Additionally, or alternatively, in any of the previous embodiments, the one or more characteristics of the ATP therapy may comprise a method of ATP therapy.

Additionally, or alternatively, in any of the previous embodiments, the one or more characteristics of the ATP therapy may comprise a number of ATP bursts applied during the ATP therapy.

Additionally, or alternatively, in any of the previous embodiments, the controller may be further configured to initiate charging of the charge storage device if the determined type of the cardiac arrhythmia is one of a second set of cardiac arrhythmia types, and wait to initiate charging of the charge storage device if the determined type of the cardiac arrhythmia is not one of the second set of cardiac arrhythmia types.

Additionally, or alternatively, in any of the previous embodiments, if an instruction was sent to initiate the application of ATP therapy by the LCP, the controller may be further configured to determine if the application of the ATP therapy by the LCP was successful in terminating the cardiac arrhythmia, and if so, not initiate charging of the charge storage device if the determined type of the cardiac arrhythmia is one of the first set of cardiac arrhythmia types.

Additionally, or alternatively, in any of the previous embodiments, if an instruction was sent to initiate the application of ATP therapy by the LCP, the controller may be further configured to determine if the application of the ATP therapy by the LCP was successful in terminating the cardiac arrhythmia, and if so, terminate the charging of the charge storage device if the determined type of the cardiac arrhythmia is one of the second set of cardiac arrhythmia types.

Additionally, or alternatively, in any of the previous embodiments, the first set of cardiac arrhythmia types may include Monomorphic Ventricular Tachycardia (MVT).

Additionally, or alternatively, in any of the previous embodiments, the second set of cardiac arrhythmia types may include one or more of Polymorphic Ventricular Tachycardia (PVT), Supra Ventricular Tachycardia (SVT), and Ventricular Fibrillation (VF).

Additionally, or alternatively, in any of the previous embodiments, the second set of cardiac arrhythmia types may include Polymorphic Ventricular Tachycardia (PVT).

Additionally, or alternatively, in any of the previous embodiments, the second set of cardiac arrhythmia types may include Supra Ventricular Tachycardia (SVT).

Additionally, or alternatively, in any of the previous embodiments, the second set of cardiac arrhythmia types may include Monomorphic Ventricular Tachycardia (MVT).

Additionally, or alternatively, in any of the previous embodiments, the first set of cardiac arrhythmia types and the second set of cardiac arrhythmia types may share one or more common cardiac arrhythmia types, but this is not required.

In yet another embodiment, an implantable cardioverter defibrillator (ICD) for delivering a defibrillation shock to a heart of a patient may comprise a charge storage device for storing a charge that can be delivered to shock the heart and a controller operatively coupled to the charge storage device. The controller may be configured to monitor cardiac activity of the heart of the patient, detect an occurrence of a cardiac arrhythmia based on the cardiac activity, and determine a type of the detected cardiac arrhythmia from two or more types of cardiac arrhythmias. If the determined type of cardiac arrhythmia is one of a first set of cardiac arrhythmia types, the controller may be configured to send an instruction for reception by a Leadless Cardiac Pacemaker (LCP) to initiate the application of ATP therapy by the LCP. If the determined type of cardiac arrhythmia is not one of the first set of cardiac arrhythmia types, the controller may not send the instruction.

Additionally, or alternatively, in the previous embodiment, the instruction may include one or more ATP parameters that define one or more characteristics of the ATP therapy.

Additionally, or alternatively, in any of the previous embodiments, the one or more characteristics of the ATP therapy may comprise a method of ATP therapy.

Additionally, or alternatively, in any of the previous embodiments, the one or more characteristics of the ATP therapy may comprise a number of ATP bursts applied during the ATP therapy.

Additionally, or alternatively, in any of the previous embodiments, the controller may be further configured to initiate charging of the charge storage device if the determined type of the cardiac arrhythmia is one of a second set of cardiac arrhythmia types, and wait to initiate charging of the charge storage device if the determined type of the cardiac arrhythmia is not one of the second set of cardiac arrhythmia types.

Additionally, or alternatively, in any of the previous embodiments, if an instruction was sent to initiate the application of ATP therapy by the LCP, the controller may be further configured to determine if the application of the ATP therapy by the LCP was successful in terminating the cardiac arrhythmia, and if so, not initiate charging of the charge storage device if the determined type of the cardiac arrhythmia is the first set of cardiac arrhythmia types.

Additionally, or alternatively, in any of the previous embodiments, if an instruction was sent to initiate the application of ATP therapy by the LCP, the controller may be further configured to determine if the application of the ATP therapy by the LCP was successful in terminating the cardiac arrhythmia, and if so, terminate the charging of the charge storage device if the determined type of the cardiac arrhythmia is one of the second set of cardiac arrhythmia types.

In still another embodiment, a method implemented by an implantable cardioverter defibrillator (ICD) may comprise determining an occurrence of a cardiac arrhythmia and determining a type of the detected cardiac arrhythmia from two or more types of cardiac arrhythmias. The method may further comprise, if the determined type of cardiac arrhythmia is one of a first set of cardiac arrhythmia types, sending an instruction for reception by a Leadless Cardiac Pacemaker (LCP) to initiate the application of ATP therapy by the LCP. Additionally, the method may also comprise, if the determined type of cardiac arrhythmia is not one of the first set of cardiac arrhythmia types, not sending the instruction to the LCP.

Additionally, or alternatively, in the previous embodiment, the method may further comprise charging the charge storage device if the determined type of the cardiac arrhythmia is one of a second set of cardiac arrhythmia types, and waiting to charge the charge storage device if the determined type of the cardiac arrhythmia is not one of the second set of cardiac arrhythmia types.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
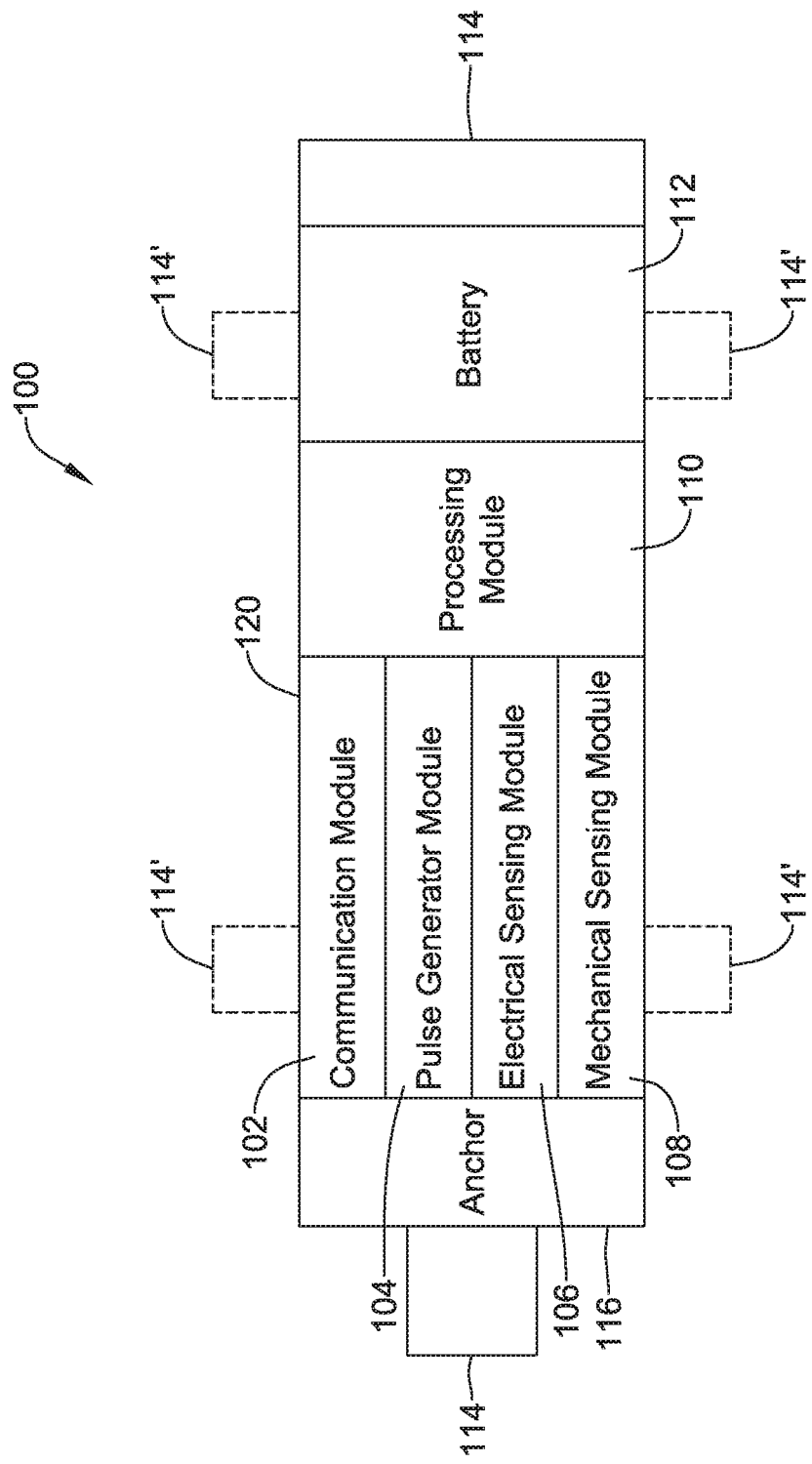
FIG. 1 is a schematic block diagram of an illustrative leadless cardiac pacemaker (LCP) according to one embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for detecting and treating cardiac arrhythmias, and more particularly, to systems, devices, and methods implementing different treatment protocols for different types of arrhythmias. One option for treating tachyarrhythmias, one type of cardiac arrhythmia, includes using anti-tachycardia therapy (ATP) techniques. Some embodiments of these techniques include delivering pacing pulses to the heart of the patient at a faster rate than the tachycardia in an effort to get the heart to track the ATP pulses, thereby terminating the physiologically induced tachycardia. If ATP therapy does not work, then other measures, such as delivering a defibrillation pulse to the heart may be employed to attempt to terminate the tachycardia. Tachycardias may be classified into a number of different types of tachycardias—including monomorphic ventricular tachycardia (MVT), polymorphic ventricular tachycardia (PVT), supra-ventricular tachycardia (SVT) and Ventricular Fibrillation (VF). ATP therapy may be more likely to be effective at terminating some of these tachycardias than other of these tachycardias. For example, ATP may be most effective at terminating MVT (perhaps 80-90% termination). Efficacy may decrease for PVT (e.g. e.g. 20-40% termination), and SVT and VF (10-20% termination). Moreover, applying ATP therapy to only certain well-suited tachyarrhythmias may help reduce acceleration of other less-suited tachyarrhythmias into the defibrillation/cardioversion zone. Accordingly, it may be beneficial to employ different therapy protocols for different types of tachycardias, as will be more fully detailed below.

FIG. 1 is a conceptual drawing of an exemplary leadless cardiac pacemaker (LCP) that may be implanted into a patient and may operate to sense physiological signals and parameters and deliver one or more types of electrical stimulation therapy to tissues of the patient. Example electrical stimulation therapy includes bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication pulses, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication pulses and/or electrical stimulation pulses, and/or may sense intrinsic cardiac electrical signals, communication pulses, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length.

As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication pulses, as used herein, may be any modulated signal that conveys information to another device, either by itself or in conjunction with one or more other modulated signals. In some embodiments, communication pulses may be limited to sub-threshold signals that do not result in capture of the heart yet still convey information. The communication pulses may be delivered to another device that is located either external or internal to the patient's body. Communication module 102 may additionally be configured to sense for communication pulses delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication pulses to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may communicating with other devices via conducted signals, radio frequency (RF) signals, optical signals, acoustic signals, inductive coupling, and/or any other suitable communication methodology.

In the embodiment shown, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In another embodiment, the electrical stimulation pulses may be defibrillation/cardioversion pulses for shocking the heart out of fibrillation. In yet another embodiment, the electrical stimulation pulses may be anti-tachycardia pacing (ATP) pulses. These are just some examples. When used to treat other ailments, the pulse generator module 104 may generate electrical stimulation pulses suitable for neurostimulation therapy or the like. Pulse generator module 104 may include one or more capacitor elements and/or other charge storage devices to aid in generating and delivering appropriate electrical stimulation pulses. In the embodiment shown, pulse generator module 104 may use energy stored in energy storage module 112 to generate the electrical stimulation pulses.

Pulse generator module 104 may include the capability to modify the electrical stimulation pulses, such as by adjusting the pulse width and/or amplitude of the electrical stimulation pulses. When pacing the heart, this may help tailor the electrical stimulation pulses to capture the heart a particular patient, sometimes with reduced battery usage. For neurostimulation therapy, adjusting the pulse width and/or amplitude may help tailor the therapy for a particular application and/or help make the therapy more effective for a particular patient.

In some embodiments, LCP 100 may include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114'. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, blood pressure sensors, heart sound sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module.

Processing module 110 may be configured to control the operation of LCP 100. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias. Processing module 110 may further receive information from communication module 102. In some embodiments, processing module 110 may additionally use such received information to determine occurrences and types of arrhythmias. However, in other embodiments, LCP 100 may use the received information instead of the signals received from electrical sensing module 106 and/or mechanical sensing module 108—for instance if the received information is more accurate than the signals received from electrical sensing module 106 and/or mechanical sensing module 108 or if electrical sensing module 106 and/or mechanical sensing module 108 have been disabled or omitted from LCP 100.

Based on a determined arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. For example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart.

Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication pulses for communicating with other devices of a system of devices. For instance, processing module 110 may control communication module 102 to generate communication pulses in particular sequences, where the specific sequences convey different information. Communication module 102 may also receive communication signals for potential action by processing module 110.

In further embodiments, processing module 110 may control switching circuitry by which communication module 102 and pulse generator module 104 deliver communication pulses and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication pulses and electrical stimulation pulses to tissue of the patient. The specific combination of one or more electrodes by which communication module 102 and/or pulse generator module 104 deliver communication pulses and electrical stimulation pulses may influence the reception of communication pulses and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any number of fixation or anchoring mechanisms. For example, anchor 116 may include one or more pins, staples, threads, screws, helix, tines, and/or the like. In some embodiments, although not shown, anchor 116 may include threads on its external surface that may run along at least a partial length of anchor 116. The threads may provide friction between the cardiac tissue and the anchor to help fix anchor 116 within the cardiac tissue. In other embodiments, anchor 116 may include other structures such as barbs, spikes, or the like to facilitate engagement with the surrounding cardiac tissue.

Figure 2:
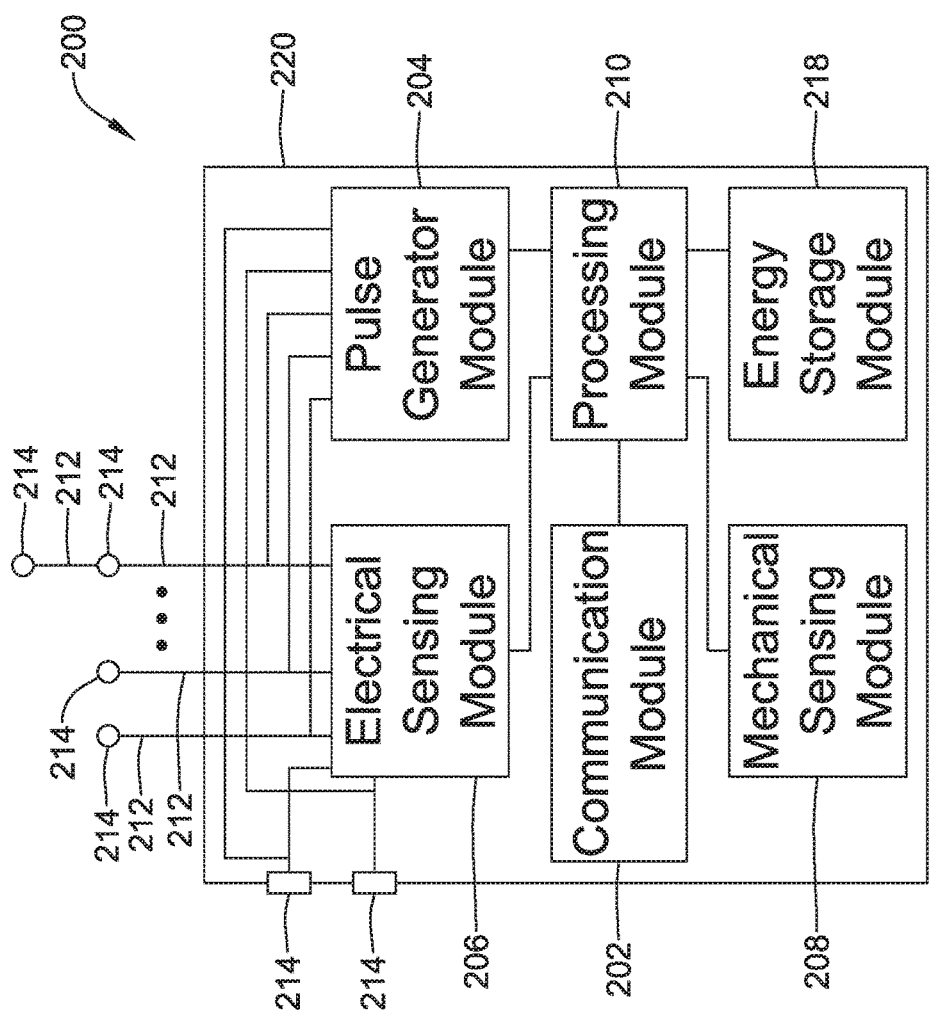
FIG. 2 is a schematic block diagram of another illustrative medical device that may be used in conjunction with the LCP of FIG. 1.

FIG. 2 depicts an embodiment of another medical device (MD) 200, which may operate to sense physiological signals and/or parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. In some embodiments, however, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). In such embodiments, MD 200 may be configured to deliver various types of electrical stimulation therapy, including, for example, defibrillation therapy.

Figure 3:
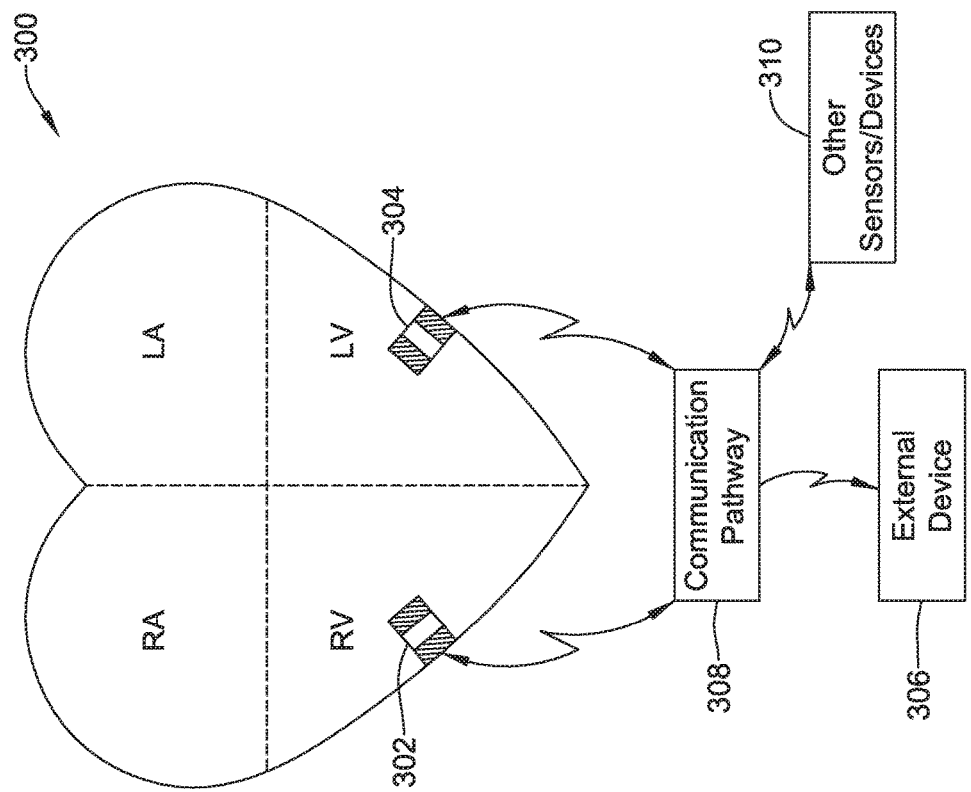
FIG. 3 is a schematic diagram of an exemplary medical system that includes multiple LCPs and/or other devices in communication with one another

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway. The command messages may cause a receiving device to take a particular action whereas response messages may include requested information or a confirmation that a receiving device did, in fact, receive a communicated message or data.

It is contemplated that the various devices of system 300 may communicate via pathway 308 using conducted signals, RF signals, inductive coupling, optical signals, acoustic signals, or any other signals suitable for communication. In some instances, the various devices of system 300 may communicate via pathway 308 using different signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306. This is just one example.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such embodiments, the delivered conducted communication signals (e.g. pulses) may differ from pacing pulses, defibrillation and/or cardioversion pulses, or other electrical stimulation therapy signals. For example, the devices of system 300 may deliver electrical communication pulses at an amplitude/pulse width that is sub-threshold (e.g. does not capture the heart, phrenic nerve, and/or other tissue). Although, in some cases, the amplitude/pulse width of the delivered electrical communication pulses may be above a capture threshold, but may be delivered during an irrelevant time period. For example, the amplitude/pulse width of the delivered electrical communication pulses may be above a capture threshold of the heart, but may be delivered during a refractory period of the heart and/or may be incorporated in or modulated onto a pacing pulse, as desired.

Delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 4:
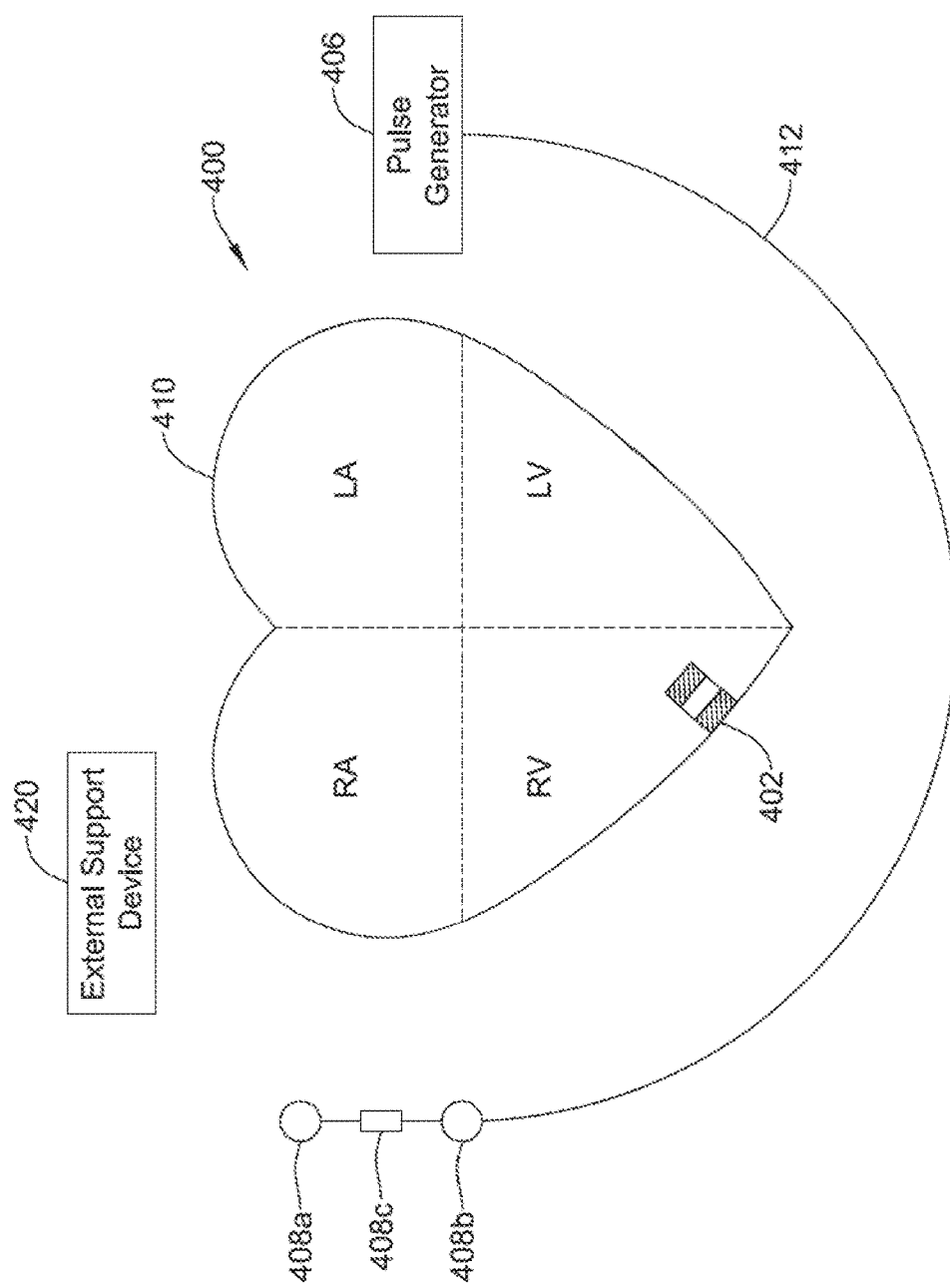
FIG. 4 is a schematic diagram of a system including an LCP and another medical device, in accordance with another embodiment of the present disclosure.
Figure 5:
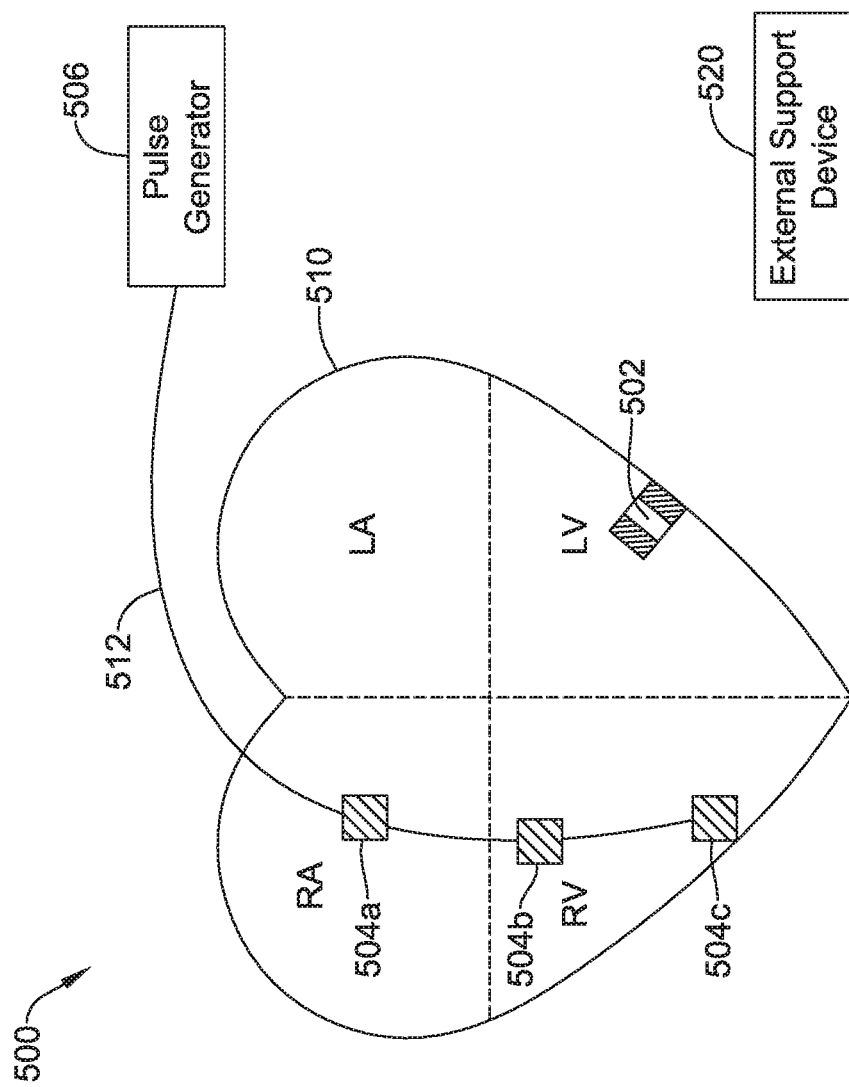
FIG. 5 is a schematic diagram of a system including a leadless cardiac pacemaker (LCP) and another medical device, in accordance with yet another embodiment of the present disclosure.

FIGS. 4 and 5 show illustrative medical device systems that may be configured to operate according to techniques disclosed herein. For example, the systems may include multiple devices that are implanted within a patient and are configured to sense physiological signals, determine occurrences of cardiac arrhythmias, and deliver electrical stimulation to treat detected cardiac arrhythmias. In FIG. 4, an LCP 402 is shown fixed to the interior of the right ventricle of the heart 410, and a pulse generator 406 is shown coupled to a lead 412 having one or more electrodes 408a-408c. In some cases, the pulse generator 406 may be part of a subcutaneous implantable cardioverter-defibrillator (SICD), and the one or more electrodes 408a-408c may be positioned subcutaneously adjacent the heart. LCP 402 may communicate with the SICD, such as via communication pathway 308. The locations of LCP 402, pulse generator 406, lead 412, and electrodes 408a-c depicted in FIG. 4 are just exemplary. In other embodiments of system 400, LCP 402 may be positioned in the left ventricle, right atrium, or left atrium of the heart, as desired. In still other embodiments, LCP 402 may be implanted externally adjacent to heart 410 or even remote from heart 410.

In FIG. 5, an LCP 502 is shown fixed to the interior of the left ventricle of the heart 510, and a pulse generator 506 is shown coupled to a lead 512 having one or more electrodes 504a-504c. In some cases, the pulse generator 506 may be part of an implantable cardiac pacemaker (ICP) and/or an implantable cardioverter-defibrillator (ICD), and the one or more electrodes 504a-504c may be positioned in the heart 510. In some cases, LCP 502 may communicate with the implantable cardiac pacemaker (ICP) and/or an implantable cardioverter-defibrillator (ICD), such as via communication pathway 308. As with FIG. 4, the locations of LCP 502, pulse generator 506, lead 512, and electrodes 504a-c depicted in FIG. 5 are just exemplary. In other embodiments of system 500, LCP 502 may be positioned in the right ventricle, right atrium, or left atrium of the heart, as desired. In still other embodiments, LCP 502 may be implanted externally adjacent to heart 510 or even remote from heart 510. Additionally, in some embodiments lead 512 and/or electrodes 504a-c may be disposed in different chambers of heart 510, or pulse generator may include additional leads and/or electrodes that are disposed within or adjacent to heart 510.

The medical device systems 400 and 500 may also include an external support device, such as external support devices 420 and 520. External support devices 420 and 520 can be used to perform functions such as device identification, device programming and/or transfer of real-time and/or stored data between devices using one or more of the communication techniques described herein. As one embodiment, communication between external support device 420 and the pulse generator 406 is performed via a wireless mode, and communication between the pulse generator 406 and LCP 402 is performed via a conducted mode. In some embodiments, communication between the LCP 402 and external support device 420 is accomplished by sending communication information through the pulse generator 406. However, in other embodiments, communication between the LCP 402 and external support device 420 may be via a communication module.

FIGS. 4-5 only illustrate a few embodiments of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406 or 506, with at least one LCP capable of delivering defibrillation therapy. Still another embodiment may include one or more LCPs implanted along with a transvenous pacemaker and with or without an implanted SICD. In yet other embodiments, the configuration or placement of the medical devices, leads, and/or electrodes may be different from those depicted in FIGS. 4 and 5. Accordingly, it should be recognized that numerous other medical device systems, different from those illustrated in FIGS. 4 and 5, may be operated in accordance with techniques disclosed herein. The embodiments systems shown in FIGS. 4 and 5 should not be viewed as limiting.

Using the system of FIG. 4 as one example, LCP 402 and the ICD (which can be a non-subcutaneously implanted device, or a subcutaneously implanted device—an SICD), which can include pulse generator 406, may determine occurrences of cardiac arrhythmias and discriminate between different types of cardiac arrhythmias. In some embodiments, the types of cardiac arrhythmias include tachyarrhythmias, and the ICD may further identify occurrences of tachyarrhythmias as specific types of tachyarrhythmias. As used herein, the term tachyarrhythmia may include ventricular fibrillation (VF). Based on the determined type of tachyarrhythmia, LCP 402 and/or the ICD may implement differing treatment protocols. By tailoring the specific treatment protocol to the different types of tachyarrhythmias, the system of LCP 402 and the ICD may more effectively conserve battery life and/or reduce the amount of unnecessary defibrillation and/or cardioversion pulses delivered to the patient—which can be a painful and scary experience for the patient.

Figure 6:
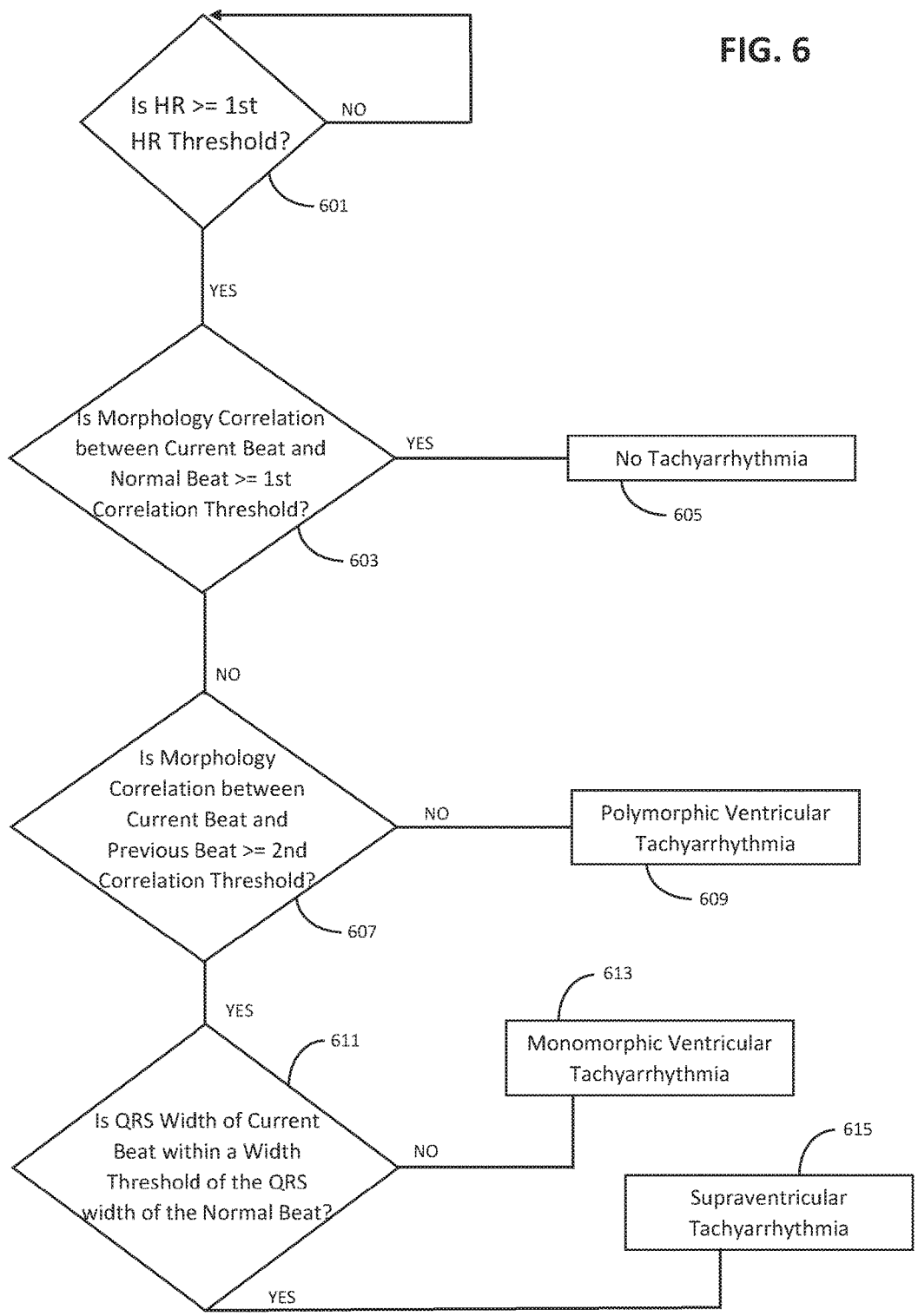
FIG. 6 is a flow diagram of an illustrative method that may be implemented by a medical device or medical device system, such as the illustrative medical devices and medical device systems described with respect to FIGS. 1-5.

In some embodiments, the ICD may operate to determine occurrences of tachyarrhythmias and types of tachyarrhythmias in accordance with the illustrative flow chart shown in FIG. 6. To determine an occurrence of a tachyarrhythmia, the ICD may first compare a detected heart rate to a first heart rate threshold, as at 601. For example, the ICD may use received cardiac electrical signals, in some embodiments in conjunction with other received physiological signals, to determine a heart rate. If the ICD determines that the heart rate is greater than or equal to the first heart rate threshold, the ICD may compare the morphology of the cardiac electrical signal of a current heart beat with the morphology of a template of a normal heart beat, as at 603. For example, the ICD may isolate a region of cardiac electrical activity surrounding a QRS complex of a current heart beat and perform a correlation analysis between the morphology of the isolated QRS complex (or part thereof) and the template containing a QRS complex (or part thereof) of a normal heart beat. If the correlation between the current beat and the template beat is greater than or equal to a first correlation threshold, the ICD may determine that there is no tachyarrhythmia present, as at 605. In these cases, the heart rate may be elevated due to exercise or stress, or some other factor, rather than due to an abnormal physiological process.

If, however, the correlation between the current heart beat and the template beat is not greater than or equal to the first correlation threshold, the ICD may then compare the morphology of the current heart beat with the morphology of one or more previous heart beats, as at 607. For example, the ICD may isolate the QRS complexes of the current heart beat and the previous heart beat and perform a correlation analysis between the morphologies of the two beats. If the correlation between the two beats is less than a second correlation threshold, the ICD may determine that the tachyarrhythmia is a polymorphic ventricular tachyarrhythmia (PVT), as at 609. However, if the correlation between the two beats is greater than or equal to the second correlation threshold, the ICD may further compare the width of the QRS complex of the current beat with the width of the QRS complex of the template normal beat, as at 611. For example, the ICD may compare the difference in QRS widths between the current beat and the template beat to a QRS width threshold. If the difference in QRS widths is greater than or equal to the QRS width threshold (indicating that the width of the QRS complex of the current beat is wider than the width of the QRS complex of the template beat by a threshold amount), the ICD may determine that the tachyarrhythmia is a monomorphic ventricular tachyarrhythmia (MVT), as at 613. However, if the ICD determines that the difference in QRS widths is less than the QRS width threshold (indicating that the width of the QRS complex of the current beat is narrower than the width of the QRS complex of the template beat), the ICD may determine that the tachyarrhythmia is a supraventricular tachyarrhythmia (SVT), as at 615.

It should be noted that the flow chart of FIG. 6 is only one embodiment in which the ICD may determine occurrences and/or discriminate types of tachyarrhythmias. For instance, in some additional embodiments, the ICD may further compare the determine heart rate to a second heart rate threshold, where the second heart rate threshold is greater than the first heart rate threshold. If the heart rate is greater than or equal to the second heart rate threshold, the ICD may determine that the heart is in ventricular fibrillation (VF). Additionally, or alternatively, in some embodiments, the ICD may additionally use the width of the current QRS complex and the width of the QRS complex of the template beat in performing the correlation analysis between the current beat and the template beat in step 607. Of course, in still other embodiments, the ICD may use different methods for determining occurrences of tachyarrhythmias and discriminating between various types of tachyarrhythmias, which may include fewer or greater numbers of steps than those listed in FIG. 6.

Where the ICD discriminates between different types of tachyarrhythmias, the ICD may coordinate with LCP 402 to implement differing treatment protocols. For example, the ICD may have stored in memory a first set of tachyarrhythmia types. If the determined tachyarrhythmia is one of the types of tachyarrhythmias in the first set of tachyarrhythmia types, the ICD may communicate an instruction to LCP 402 to initiate application of ATP therapy. In some cases, the ICD may also wait to initiate charging of its charge storage device for delivery of defibrillation and/or cardioversion therapy. The ICD may then monitor the cardiac electrical signals to determine if the ATP therapy delivered by LCP 402 terminates the tachyarrhythmia. If the ICD determines that the tachyarrhythmia was not terminated by the ATP, the ICD may initiate charging of its charge storage device and deliver defibrillation and/or cardioversion therapy once the charge is complete. In determining whether the delivery of ATP therapy has terminated the tachyarrhythmia, the ICD may determine the current heart rate and compare it to a threshold or compare it to the heart rate at the time the tachyarrhythmia was detected. If the heart rate is less than the comparison heart rate, the ICD may determine that the tachyarrhythmia was terminated. In other embodiments, the ICD may perform the process detailed in FIG. 6 to determine if the ATP therapy terminated the tachyarrhythmia.

In embodiments where the types of tachyarrhythmias in the first set of tachyarrhythmia types are types that are likely to be susceptible to ATP therapy, the ICD may conserve energy by waiting to charge its charge storage device until after confirmation that the ATP therapy failed to terminate the tachyarrhythmia. In some embodiments, the types of tachyarrhythmia in the first set of tachyarrhythmia types may include MVT. However, in other embodiments, PVT may also be included in the first set of tachyarrhythmia types. In still other embodiments, SVT and/or VF may also be included in the first set of tachyarrhythmia types. These are just examples.

In embodiments where the type of tachyarrhythmia is not one of the tachyarrhythmias in the first set of tachyarrhythmia types, the ICD may not send the instruction to LCP 402 to initiate ATP therapy. Instead, the ICD may initiate charging of the charge storage device and deliver defibrillation and/or cardioversion therapy once the charging is complete. In some embodiments, VF may be excluded from the first set of tachyarrhythmia types. In some embodiments, PVT and/or SVT may be excluded from the first set of tachyarrhythmia types.

In some instances, the ICD may alter the treatment protocol based on the determined type of tachyarrhythmia. For instance, if the ICD determines that the tachyarrhythmia is one of the tachyarrhythmia types in the first set of tachyarrhythmia types, the ICD may send the instruction to LCP 402 to initiate ATP therapy but also begin charging its charge storage device for delivery of defibrillation and/or cardioversion therapy. This may best be applied when the determined type of tachyarrhythmia has some non-trivial chance that ATP therapy would terminate the tachyarrhythmia, but is still un-likely to be successful. The ICD may monitor the cardiac electrical activity while charging the charge storage device and while LCP 402 is delivering ATP therapy. If delivery of ATP therapy does actually terminate the tachyarrhythmia, the ICD may terminate the charging of its charge storage device, and then subsequently slowly leak off the accumulated charge without performing defibrillation and/or cardioversion therapy. In such embodiments, the ICD may save some energy by not unnecessarily fully charging its charge storage device, and may also not harm or scare the patient by delivering an unnecessary defibrillation and/or cardioversion pulse. If delivery of ATP therapy fails to terminate the tachyarrhythmia, the ICD may continue to fully charge the charge storage device and perform defibrillation and/or cardioversion therapy. In these embodiments, the ICD has saved time between the detection of the tachyarrhythmia and the delivery of the defibrillation and/or cardioversion therapy by initiating charging of its charge storage device earlier than if the determined tachyarrhythmia was one of the first set of tachyarrhythmia types. In some embodiments, the charge storage device may begin charging, without first waiting for ATP therapy, when the tachyarrhythmia is a PVT or SVT type tachyarrhythmia. In other embodiments, the charge storage device may begin charging, without first waiting for ATP therapy, when the tachyarrhythmia is a MVT and/or VF.

In additional or alternative embodiments, the instruction sent to LCP 402 to initiate ATP therapy may include one or more ATP parameters that define one or more characteristics of the ATP therapy. For example, the instruction may specify a number of ATP therapy attempts that are to be attempted by LCP 402 before terminating the ATP therapy protocol. For instance, if the tachyarrhythmia type is a first type of tachyarrhythmia, the ICD may communicate an instruction that LCP 402 should attempt a defined ATP therapy two, or three, or five, or any other suitable number of times. Each attempt may include applying a plurality of spaced ATP pulses to the heart. If the tachyarrhythmia type is a second type of tachyarrhythmia, different and distinguishable from the first type of tachyarrhythmia, the ICD may communicate an instruction that LCP 402 should only provide one ATP therapy attempt. For example, for MVT, ATP therapy may be applied in multiple bursts (sometimes as programmed by a clinician) and more time may be allowed to terminate the tachyarrhythmia given the higher chance of success for ATP therapy when applied to MVT, whereas for other types of tachyarrhythmia (e.g. PVT, SVT and/or VF), it may be more appropriate to apply a single burst (single ATP attempt) to help reduce the time to defibrillation and/or cardioversion therapy given the lower chance of success for ATP therapy.

In some cases, the charge storage device of the ICD may be charged in parallel with the ATP therapy delivered by the LCP 402. In these cases, the instruction sent to LCP 402 may command LCP 402 to perform a number of ATP therapy attempts that tend to fill up the time it takes the ICD to charge its charge storage device. In other instances, each instruction the ICD sends to LCP 402 commanding LCP 402 to perform ATP therapy may instruct LCP 402 to perform a single ATP attempt. Then, if the ICD determines that the ATP attempt did not terminate the detected tachyarrhythmia, the ICD may communicate an additional instruction to LCP 402 to perform another ATP attempt. In such instances, the result may be that the ICD may communicate a different number of instructions for delivery of ATP therapy, depending on whether the ATP therapy was successful or not.

The instructions sent by the ICD to the LCP 402 commanding LCP 402 to perform ATP may define one or more characteristics of the ATP therapy. Example parameters may include a number of ATP bursts—e.g. ATP pulses—to be delivered by LCP 402 during each ATP therapy attempt. This parameter may be in addition to the number of ATP therapy attempts or an alternative. In some embodiments, the number of ATP pulses may be specified differently for each ATP therapy attempt, where LCP 402 is instructed to perform multiple ATP therapy attempts. Also, the number of ATP pulses may be specified differently depending on the determined type of tachyarrhythmia. Additionally, in embodiments where the instruction to LCP 402 includes a number of ATP therapy attempts, the instructions may, in some embodiments, further include specific rates of ATP pulse delivery during each ATP therapy attempt. As with the number of ATP pulses in each attempt, the rates of ATP pulse delivery may differ between ATP therapy attempts and/or depending on the detected tachyarrhythmia type. Additionally, or alternatively, the instructions may specify a length of a break period between ATP therapy attempts. Other example parameters may include a pulse amplitude and/or a pulse width of the ATP pulses to be delivered during each ATP therapy attempt. As with the other parameters, the instructions may specify different amplitudes and/or pulse widths for each ATP therapy attempt and/or based on the determined type of tachyarrhythmia.

The instructions sent by the ICD to the LCP 402 commanding LCP 402 to perform ATP may additionally, or alternatively, include an instruction to perform ATP according one of a number of methods. According to a burst method, LCP 402 may deliver consecutive electrical stimulation pulses with a constant time interval between each electrical stimulation pulse. Additionally, when delivering ATP according to the burst method, LCP 402 may deliver each sequence of electrical stimulation pulses with a constant time interval between each of the sequences of electrical stimulation pulses. In another method, the ramp method, LCP 402 may deliver electrical stimulation pulses within a sequence of electrical stimulation pulses, or ATP therapy attempt, with a decreasing time interval between each pair of successive electrical stimulation pulses. In yet another method, the scan method, LCP 402 may deliver sequences of electrical stimulation pulses, or ATP therapy attempts, with a time interval between electrical stimulation pulses within each sequence of electrical stimulation pulses that decreases for each successive sequence of electrical stimulation pulses. In still another method, the ramp/scan method, LCP 402 may deliver ATP therapy according to the features of both the ramp method and the scan method.

In embodiments where the ICD includes an instruction to perform ATP according to specific method, the specific method may depend at least partially on the type of cardiac arrhythmia. For instance, if the arrhythmia is one of the first set of arrhythmia types, the ICD may communicate a message to LCP 402 to perform ATP therapy according to the burst method. However, if the arrhythmia type is one of the second set of arrhythmia types, the ICD may communicate a message to LCP 402 to perform ATP therapy according to the ramp method. Of course, in other embodiments, the type of method associated with each arrhythmia type may differ and may be any of the burst, ramp, scan, or ramp/scan methods.

In some embodiments, the types of tachyarrhythmias in the first and second sets of tachyarrhythmia types may be user programmable. For instance, as described with respect to FIG. 4, the ICD, including pulse generator 406, may be able to communicate with external support device 420, which in some embodiments may act as a programmer. A clinician may interact with the programmer to specify which tachyarrhythmias types are to be included in each of the first and second sets of tachyarrhythmia types, and which tachyarrhythmia types are not in either set. In some cases, the first set of cardiac arrhythmia types and the second set of cardiac arrhythmia types may be the same cardiac arrhythmia types. In other cases, the first set of cardiac arrhythmia types and the second set of cardiac arrhythmia types may be mutually exclusive. In other cases, the first set of cardiac arrhythmia types and the second set of cardiac arrhythmia types may share one or more common cardiac arrhythmia types.

In some embodiments, the types of tachyarrhythmias in the first and second sets of tachyarrhythmia types may depend at least partially on the level of charge in the energy storage module that powers the ICD. For example, the ICD may determine a percentage of remaining energy capacity of energy storage module 218. The ICD may begin with, for example, MVT and PVT in the first set of tachyarrhythmia types, and PVT in the second set of tachyarrhythmia types. That is, if either MVT or PVT is detected, the ICD may send an instruction to the LCP 402 to initiate the application of ATP therapy by the LCP 402. If PVT is detected, the ICD may initiate charging of the charge storage device, and if MVT is detected, the ICD may wait on initiating charging of the charge storage device until ATP is given a chance to terminate the tachyarrhythmia. Once the ICD determines that the percentage of capacity of remaining energy storage module 218 has dropped below, for example, fifty percent, the ICD may recommend and/or automatically remove PVT from the first set of tachyarrhythmia types. Then, if the ICD detects PVT, the ICD may not send an instruction to the LCP 402 to initiate the application of ATP therapy by the LCP 402. Removing PVT from the first set of tachyarrhythmia types may help increase the remaining life of the battery of the ICD by not performing ATP therapy in cases wherein ATP therapy is less likely to be successful (e.g. PVT verses MVT). This is just one example. In other embodiments, different types of tachyarrhythmias may be moved, added or deleted from each of the sets. In some cases, one or more thresholds may be used for adjusting which tachyarrhythmia types are in each set of tachyarrhythmia types.

Figure 7:
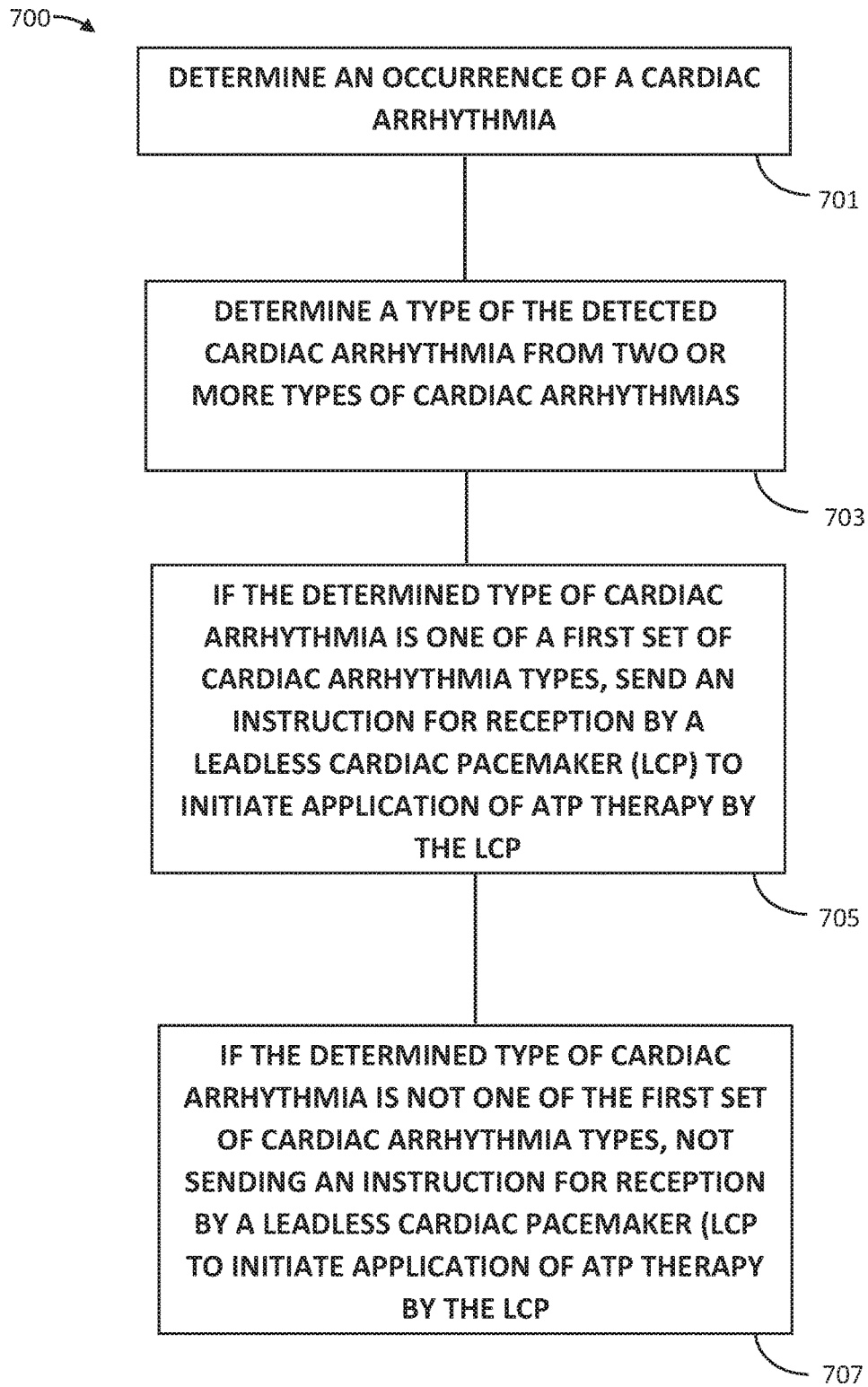
FIG. 7 is a flow diagram of an illustrative method that may be implemented by a medical device or medical device system, such as the illustrative medical devices and medical device systems described with respect to FIGS. 1-5.

FIG. 7 is a flow diagram of an illustrative method 700 that may be implemented by a medical device, such as that shown in FIG. 2, which in some embodiments may be an ICD. Although the method of FIG. 7 will be described with respect to MD 200, the illustrative method of FIG. 7 may be performed by any suitable medical device or medical device system.

In some embodiments, MD 200 may determine an occurrence of a cardiac arrhythmia, as shown at 701. In some cases, MD 200 may determine an occurrence of a cardiac arrhythmia, and specifically a tachyarrhythmia, according to the flow diagram of FIG. 6. However, in other embodiments, MD 200 may use additional or alternative techniques to determine an occurrence of a cardiac arrhythmia. After determining an occurrence of a cardiac arrhythmia, MD 200 may determine a type of the detected cardiac arrhythmia from two or more types of cardiac arrhythmias, as shown at 703. For example, MD 200 may discriminate between two or more different cardiac arrhythmias types. In embodiments where MD 200 discriminates between different types of tachyarrhythmias, MD 200 may operate according to a method detailed in FIG. 6. However, in other embodiments, MD 200 may operate differently than described with respect to FIG. 6 to discriminate between tachyarrhythmia types.

After determining a type of cardiac arrhythmia, MD 200 may, if the determined type of cardiac arrhythmia is one of a first set of cardiac arrhythmia types, send an instruction for reception by a Leadless Cardiac Pacemaker (LCP) to initiate the application of ATP therapy by the LCP, as shown at 705. In some embodiments, the instruction may include one or more parameters that define a characteristic of the ATP therapy. Some example parameters include a number of ATP therapy attempts, a number of ATP bursts in each ATP therapy attempt, a length of a break between ATP therapy attempts, an amplitude and/or pulse width of each ATP burst, among other parameters. If the determined type of cardiac arrhythmia is not one of the first set of cardiac arrhythmia types, MD 200 may not send the instruction to the LCP, as shown at 707.

In some additional or alternative embodiments, MD 200 may further begin charging a charge storage device (for instance, a charge storage device that may be a part of pulse generator module 204) if the determined type of the cardiac arrhythmia is one of a second set of cardiac arrhythmia types in addition to sending the instruction. However, if the determined type of tachyarrhythmia is not one of the second set of cardiac arrhythmia types, MD 200 may wait to charge the charge storage device until after confirming that the delivered ATP therapy failed to terminate the tachyarrhythmia.

Figure 8:
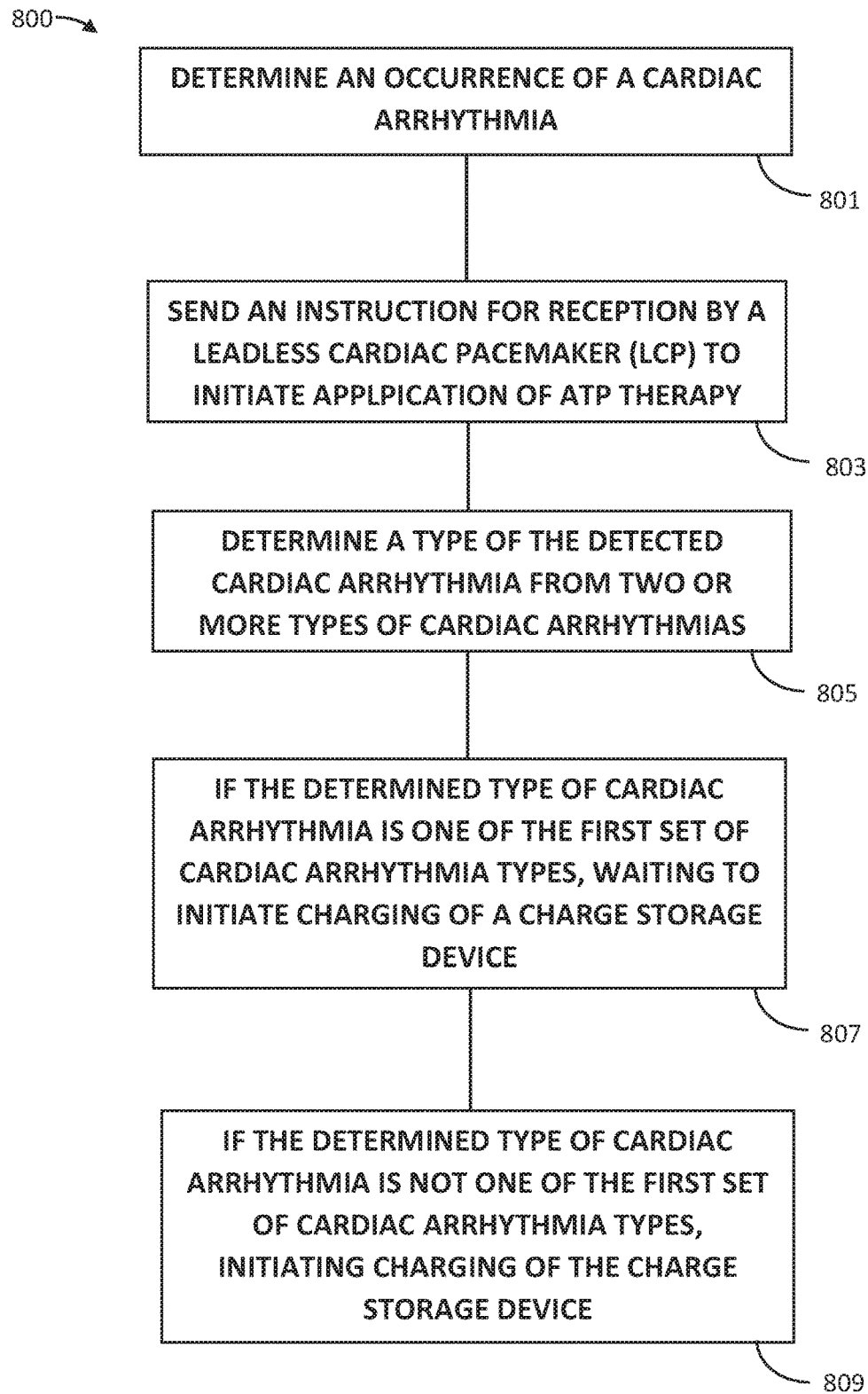
FIG. 8 is a flow diagram of an illustrative method that may be implemented by a medical device or medical device system, such as the illustrative medical devices and medical device systems described with respect to FIGS. 1-5.

FIG. 8 is a flow diagram of an illustrative method 800 that may be implemented by a medical device, such as that shown in FIG. 2, which in some embodiments may be an ICD. Although the method of FIG. 8 will be described with respect to MD 200, the illustrative method of FIG. 8 may be performed by any suitable medical device or medical device system.

In some embodiments, MD 200 may determine an occurrence of a cardiac arrhythmia, as shown at 801. In some cases, MD 200 may determine an occurrence of a cardiac arrhythmia, and specifically a tachyarrhythmia, according to the flow diagram of FIG. 6. However, in other embodiments, MD 200 may use additional or alternative techniques to determine an occurrence of a cardiac arrhythmia. After determining an occurrence of a cardiac arrhythmia, MD 200 send an instruction for reception by a Leadless Cardiac Pacemaker (LCP) to initiate application of ATP therapy, as at 803.

After sending the instruction, MD 200 may determine a type of the detected cardiac arrhythmia from two or more types of cardiac arrhythmias, as shown at 805. For example, MD 200 may discriminate between two or more different cardiac arrhythmias types. In embodiments where MD 200 discriminates between different types of tachyarrhythmias, MD 200 may operate according to a method detailed in FIG. 6. However, in other embodiments, MD 200 may operate differently than described with respect to FIG. 6 to discriminate between tachyarrhythmia types.

After determining a type of cardiac arrhythmia, MD 200 may, if the determined type of cardiac arrhythmia is one of a first set of cardiac arrhythmia types, wait to initiate charging of its charge storage device, as shown at 807. For instance, MD 200 may monitor received electrical cardiac signals during and after delivery of ATP therapy by the LCP. In these embodiments, MD 200 may attempt to save battery energy by waiting until confirming that the delivery of ATP therapy did not terminate the tachycardia. Once MD 200 has confirmed that delivery of ATP therapy has failed to terminate the tachycardia, MD 200 may initiate charging of its charge storage device for delivery of defibrillation and/or cardioversion therapy. In instances where delivery of ATP therapy did terminate the tachycardia, MD 200 has saved energy by not charging its charge storage device.

However, if the determine type of cardiac arrhythmia is not one of the first set of cardiac arrhythmia types, MD 200 may initiate charging of its charge storage device, as shown at 809. In some embodiments, while charging its charge storage device, MD 200 may monitor received cardiac electrical signals. MD 200 may determine, based at least in part on the received signals, whether delivery of ATP therapy by the LCP has terminated the tachycardia. If MD 200 determines that the delivery of ATP therapy has terminated the tachycardia, MD 200 may cease charging its charge storage device. MD 200 may then slowly leak off the accumulated charge. However, if MD 200 determines that the delivery of ATP therapy has not terminated the tachycardia, MD 200 may deliver defibrillation and/or cardioversion therapy once charging of its charge storage device is complete.

The above description of determining occurrences of tachyarrhythmias and discriminating between the various tachyarrhythmia types used a system including an ICD/SICD and an LCP as an example only. In other embodiments, other devices may be used as part of the system implementing the disclosed techniques. In still other embodiments, a system implementing the disclosed techniques may include additional devices. In such embodiments, determining occurrences of tachyarrhythmias, discriminating between the different types of tachyarrhythmias, communicating instructions, delivering ATP therapy, and/or delivering defibrillation/cardioversion therapy may be coordinated between the devices, as desired.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules. Accordingly, departure in form and detail may be made without departing from the scope and spirit of the present disclosure as described in the appended claims.

What is claimed is:

1. An implantable cardioverter defibrillator (ICD) for delivering a defibrillation shock to a heart of a patient, the ICD comprising:

two or more electrodes;

a charge storage device for storing a charge that can be delivered to shock the heart via two or more of the electrodes;

a controller operatively coupled to two or more of the electrodes and the charge storage device, the controller configured to:
  identify an occurrence of a cardiac arrhythmia;
  in response to identifying an occurrence of a cardiac arrhythmia:
    determine whether the identified cardiac arrhythmia is of a first type of cardiac arrhythmia;
    wait to initiate charging of the charge storage device of the ICD when the identified cardiac arrhythmia is of the first type of cardiac arrhythmia;
    initiate charging of the charge storage device of the ICD when the identified cardiac arrhythmia is not of the first type of cardiac arrhythmia; and
    send an instruction intended for reception by a Leadless Cardiac Pacemaker (LCP), the instruction adapted to instruct the LCP to initiate application of an Anti-Tachyarrhythmia Pacing (ATP) therapy by the LCP while charging or while waiting to charge the charge storage device of the ICD.

2. The ICD of claim 1, wherein when the identified cardiac arrhythmia is not of the first type of cardiac arrhythmia, and the instruction was sent to initiate application of an Anti-Tachyarrhythmia Pacing (ATP) therapy by the LCP, the controller is configured to determine whether the ATP therapy terminated the identified cardiac arrhythmia, and:
  when the ATP therapy terminated the identified cardiac arrhythmia, terminate the charging of the charge storage device of the ICD; and
  when the ATP therapy did not terminate the identified cardiac arrhythmia, continue to charge the charge storage device of the ICD until charged, and then release charge from the charge storage device to deliver a shock to the heart.

3. The ICD of claim 1, wherein when the identified cardiac arrhythmia is of the first type of cardiac arrhythmia, and the instruction was sent to initiate application of an Anti-Tachyarrhythmia Pacing (ATP) therapy by the LCP, the controller is configured to determine whether the ATP therapy terminated the identified cardiac arrhythmia, and:
  when the ATP therapy terminated the identified cardiac arrhythmia, cease waiting and not initiating the charging of the charge storage device of the ICD; and
  when the ATP therapy did not terminate the identified cardiac arrhythmia, cease waiting and initiate charging of the charge storage device of the ICD until charged, and then release charge from the charge storage device to deliver a shock to the heart.

4. The ICD of claim 1, wherein the first type of cardiac arrhythmia is a Monomorphic Ventricular Tachyarrhythmia (MVT).

5. The ICD of claim 1, wherein the controller is configured to:
  determine whether the identified cardiac arrhythmia is of the first type of cardiac arrhythmia or a second type of cardiac arrhythmia; and
  in response to identifying an occurrence of the identified cardiac arrhythmia, the controller is configured to send the instruction for reception by a Leadless Cardiac Pacemaker (LCP) to initiate application of the ATP therapy by the LCP when the identified cardiac arrhythmia is of the first type of cardiac arrhythmia but not when the identified cardiac arrhythmia is of the second type of cardiac arrhythmia.

6. The ICD of claim 5, wherein the first type of cardiac arrhythmia is a Monomorphic Ventricular Tachyarrhythmia (MVT) and the second type of cardiac arrhythmia is a Polymorphic Ventricular Tachyarrhythmia (PVT).

7. The ICD of claim 5, wherein the first type of cardiac arrhythmia is a Monomorphic Ventricular Tachyarrhythmia (MVT) and the second type of cardiac arrhythmia is a Supra Ventricular Tachyarrhythmia (SVT).

8. The ICD of claim 1, wherein the controller is configured to:
  determine whether the identified cardiac arrhythmia is of the first type of cardiac arrhythmia or a second type of cardiac arrhythmia; and
  in response to identifying an occurrence of the identified cardiac arrhythmia, the controller is configured to send the instruction intended for reception by a Leadless Cardiac Pacemaker (LCP) to initiate application of the ATP therapy by the LCP when the identified cardiac arrhythmia is of the first type of cardiac arrhythmia and when the identified cardiac arrhythmia is of the second type of cardiac arrhythmia.

9. The ICD of claim 1, wherein in response to identifying an occurrence of the identified cardiac arrhythmia, the controller is configured to send the instruction intended for reception by a Leadless Cardiac Pacemaker (LCP) to initiate application of the ATP therapy by the LCP only when the identified cardiac arrhythmia is of the first type of cardiac arrhythmia.

10. The ICD of claim 9, wherein the first type of cardiac arrhythmia is a Monomorphic Ventricular Tachyarrhythmia (MVT).

11. The ICD of claim 1, wherein the ICD is a Subcutaneous Implantable Cardioverter Defibrillator (SICD).

12. An implantable cardioverter defibrillator (ICD) for delivering a defibrillation shock to a heart of a patient, the ICD comprising:
  two or more electrodes;
  a charge storage device for storing a charge that can be delivered to shock the heart via two or more of the electrodes;
  a controller operatively coupled to two or more of the electrodes and the charge storage device, the controller configured to:
    identify an occurrence of a cardiac arrhythmia;
    in response to identifying an occurrence of a cardiac arrhythmia:
      determine whether the identified cardiac arrhythmia is not of one or more predetermined types of cardiac arrhythmias;
      wait to initiate charging of the charge storage device of the ICD when the identified cardiac arrhythmia is determined not to be of the one or more predetermined types of cardiac arrhythmias;
      initiate charging of the charge storage device of the ICD when the identified cardiac arrhythmia is not determined to be not of the one or more predetermined types of cardiac arrhythmias; and
      send an instruction intended for reception by a Leadless Cardiac Pacemaker (LCP), the instruction adapted to instruct the LCP to initiate application of an ATP therapy by the LCP while charging or while waiting to charge the charge storage device of the ICD.

13. The ICD of claim 12, wherein the controller is configured to send an instruction for reception by a Leadless Cardiac Pacemaker (LCP) to initiate application of an ATP therapy by the LCP when the identified cardiac arrhythmia is determined not to be of the one or more predetermined types of cardiac arrhythmias.

14. The ICD of claim 12, wherein the one or more predetermined types of cardiac arrhythmias comprises a Polymorphic Ventricular Tachyarrhythmia (PVT).

15. The ICD of claim 12, wherein the one or more predetermined types of cardiac arrhythmias comprises a Supra Ventricular Tachyarrhythmia (SVT).

16. The ICD of claim 12, wherein the one or more predetermined types of cardiac arrhythmias comprises a Polymorphic Ventricular Tachyarrhythmia (PVT) and a Supra Ventricular Tachyarrhythmia (SVT).

17. The ICD of claim 12, wherein when the identified cardiac arrhythmia is not of the one or more predetermined types of cardiac arrhythmias, the controller is further configured to determine whether the ATP therapy terminated the identified cardiac arrhythmia, and:
   when the ATP therapy terminated the identified cardiac arrhythmia, cease waiting and not initiating the charging of the charge storage device of the ICD; and
   when the ATP therapy did not terminate the identified cardiac arrhythmia, cease waiting and initiate charging of the charge storage device of the ICD until charged, and then release charge from the charge storage device to deliver a shock to the heart.

18. A method implemented by an implantable cardioverter defibrillator (ICD), wherein the ICD includes a charge storage device for storing a charge that can be delivered to shock the heart of a patient, the method comprising:
   determining an occurrence of a cardiac arrhythmia;
   determining whether the identified cardiac arrhythmia has one or more predetermined characteristics;
   waiting to initiate charging of the charge storage device of the ICD when the identified cardiac arrhythmia is determined to have the one or more predetermined characteristics; and
   initiating charging of the charge storage device of the ICD when the identified cardiac arrhythmia is determined to not have the one or more predetermined characteristics; and
   after the identified cardiac arrhythmia is determined, sending an instruction intended for reception by a Leadless Cardiac Pacemaker (LCP) adapted to instruct the LCP to deliver an Anti-Tachyarrhythmia Pacing (ATP) therapy while the ICD charges or waits to charge the charge storage device of the ICD.

19. The method of claim 18, wherein the waiting step waits to initiate charging of the charge storage device of the ICD while the ATP therapy is applied.

20. The method of claim 19 further comprising:
   determining whether the ATP therapy terminated the identified cardiac arrhythmia, and:
   when the ATP therapy terminated the identified cardiac arrhythmia, cease waiting and not initiating the charging of the charge storage device of the ICD; and
   when the ATP therapy did not terminate the identified cardiac arrhythmia, cease waiting and initiate charging of the charge storage device of the ICD until charged, and then release charge from the charge storage device to deliver a shock to the heart.

* * * * *